(12) United States Patent
Ellmerer-Müller et al.

(10) Patent No.: US 6,583,265 B1
(45) Date of Patent: Jun. 24, 2003

(54) CYCLOSPORINS

(75) Inventors: Ernst Ellmerer-Müller, Innsbruck (AT); Dagmar Brössner, Innsruck (AT); Najib Maslouh, Innsbruck (AT); Horst Dieter Ambrosi, Berlin (DE); Gerhard Jas, Berlin (DE); Gunter Fischer, Halle/Saale (DE)

(73) Assignee: C-Chem AG, Binningen (CH)

( * ) Notice: Subject to any disclaimer, the term of this patent is extended or adjusted under 35 U.S.C. 154(b) by 0 days.

(21) Appl. No.: 09/701,542

(22) Filed: Jan. 8, 2001

(30) Foreign Application Priority Data

Jun. 12, 1998 (EP) .............................................. 98110761

(51) Int. Cl.$^7$ ................................................. C07K 7/64
(52) U.S. Cl. ........................ 530/317; 530/327; 530/345; 514/2; 514/11; 514/15
(58) Field of Search ................................ 530/317, 327, 530/345; 514/2, 11, 15

(56) References Cited

U.S. PATENT DOCUMENTS 5,948,884 A  9/1999  Lüchinger ................... 530/317

FOREIGN PATENT DOCUMENTS

EP  0 194 972  9/1986

OTHER PUBLICATIONS

Pearson, Arthritis and Rheumatism 2, 440–459, 1959.*
Seebach, D. et al., Helvetica Chimica ACTA, 76 (No. 4), pp. 1564–1690, Jan. 1, 1993.

* cited by examiner

*Primary Examiner*—Christopher S. F. Low
*Assistant Examiner*—David Lukton
(74) *Attorney, Agent, or Firm*—Wenderoth, Lind & Ponack, L.L.P.

(57) ABSTRACT

The present invention relates to novel cyclosporins, processes for their preparation, their use as pharmaceuticals and pharmaceutical compositions comprising them. The novel cyclosporins are represented by the compound of formula I

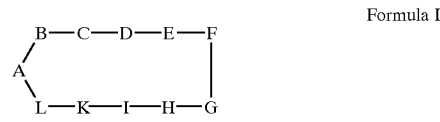

Formula I or a pharmaceutically acceptable salt thereof, wherein the letters A to L represent residues of amino acids.

13 Claims, No Drawings

CYCLOSPORINS

BACKGROUND OF THE INVENTION

1. Field of the Invention

The present invention relates to novel cyclosporins, processes for their production, their use as pharmaceuticals and pharmaceutical compositions comprising them. Furthermore, this invention discloses a novel general method for the exchange of substituents at the sarcosine residue of the cyclosporin macrocycle.

2. Description of the Related Art

Cyclosporin A is well known for its immunosuppressive and antiinflammatory properties but many biological properties have been described in addition. EP 0 194 972 describes cyclosporin derivatives with substituents on the sarcosine in position 3 of the macrocycle, the introduction of such substituents, as well as the immunosuppressive, anti-inflammatory and antiparasitic activity of these cyclosporin derivatives. EP 0 484 281 describes cyclosporin derivatives with reduced immuno-suppressive potency and activity against HIV.

The present invention discloses novel cyclosporins which can be used for the treatment of infectious diseases, of chronic inflammatory and autoimmune diseases, to prevent cardiac hypertrophy, to treat and prevent ischemia and reperfusion injury, to treat neurodegenerative diseases, and to induce processes of tissue regeneration.

SUMMARY OF THE INVENTION

A second embodiment of the present invention is a novel method to prepare cyclosporins with substituents at the sarcosine in position 3 of the macrocycle. EP 0 194 972 describes the introduction of certain substituents at the sarcosine. The method described in EP 0 194 972 involves treatment of a cyclosporin with strong base to generate a polyanion and subsequent reaction of this polyanion with electrophiles, such as disulfides, alkyl halides or other suitable alkylating agents. Halogens or sources of positive halogen can also be used, as well as aldehydes. There is no example in the prior art which describes the exchange of such a substituent by another. The present invention discloses such a method. In this novel method, a suitable substituent is first introduced into a cyclosporin polyanion and the resulting product is isolated. The substituent is subsequently activated to become a leaving group and replaced by the desired novel substituent. This novel method allows the introduction of a wide variety of substituents into the sarcosine residue of the cyclosporin macrocycle.

The cyclosporin nomenclature and numbering systems used hereafter are those used by J. Kallen et al., "Cyclosporins: Recent Developments in Biosynthesis, Pharmacology and Biology, and Clinical Applications", Biotechnology, second edition, H.-J. Rehm and G. Reed, ed., 1997, p535–591 and are shown below:

| Position numbering | Letter in Formula | Amino acid in cyclosporin A |
|---|---|---|
| 1 | A | N-Methyl-butenyl-threonine (MeBmt) |
| 2 | B | α-aminobutyric acid (Abu) |
| 3 | C | Sarcosine (Sar) |
| 4 | D | N-Methyl-leucine (MeLeu) |
| 5 | E | Valine (Val) |
| 6 | F | N-Methyl-leucine (MeLeu) |
| 7 | G | Alanine (Ala) |
| 8 | H | (D)-Alanine ((D)-Ala) |
| 9 | I | N-Methyl-leucine (MeLeu) |
| 10 | K | N-Methyl-leucine (MeLeu) |
| 11 | L | N-Methylvaline (MeVal) |

Objects of the present invention are therefore compounds of the formula I

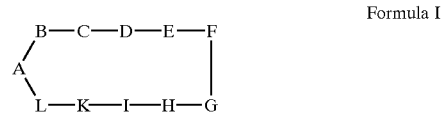

Formula I and their pharmaceutically acceptable salts wherein the letters A to L represent residues of the following amino acids:

A (L)-alpha-N-methylamino-beta-hydroxy acid of the formula II,

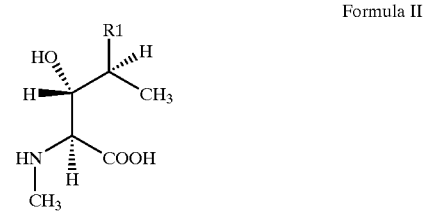

Formula II wherein R1 is (E)-2-butenyl-1,

B alpha-amino-butyric acid, alpha-amino-valerianic acid (norvaline), threonine, or valine, C substituted sarcosine of the formula III

Formula III in which x is

S—(O)$_n$—R2, in which n has the value zero, one or two, and R2 is hydrogen, unsubstituted or substituted, unbranched or branched, acyclic, monocyclic or polycyclic, saturated or unsaturated lower alkyl, substituted or unsubstituted aryl or heteroaryl, or X is O—R3, in which R3 is hydrogen, unsubstituted or substituted, unbranched or branched, saturated or unsaturated, acyclic, monocyclic or polycyclic lower alkyl, or acyl, or X is sulfonium groups of the formula IV,

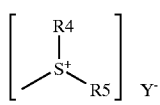

Formula IV in which R4 and R5 are independently selected from lower alkyl, aryl, or heteroaryl and Y⁻ is an anion, or X is a group of the formula V,

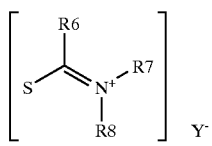

Formula V in which R6 and R7 are independently selected from lower alkyl or aryl or form together a ring and R8 is hydrogen or substituted or unsubstituted lower alkyl and Y⁻ is an anion, or C is a residue of the formula VI and Y⁻ is an anion,

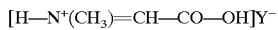

Formula VI

D N-methyl-leucine, gamma-hydroxy-N-methyl-leucine, N-methyl-valine, or N-methyl-isoleucine, E valine, F N-methyl-leucine, G alanine, H glycine, (D)-alanine, (D)-serine, O-hydroxyethyl-(D)-serine, I,K N-methyl-leucine, and L N-methyl-valine.

DESCRIPTION OF THE PREFERRED EMBODIMENTS

The (E)-2-butenyl-1 rest in A has preferrably the trans configuration.

Examples for lower alkyl are methyl, ethyl, propyl, isopropyl, n-butyl, sec-butyl, isobutyl, tert-butyl, 1-pentyl, 2-pentyl, 3-pentyl, isopentyl, tert-pentyl, neopentyl, hexyl and its isomers.

Examples for monocyclic lower alkyl groups are cyclopropyl, cyclobutyl, cyclopentyl, cyclohexyl.

Examples for polycyclic lower alkyl groups are bicylo[2.1.1]hexyl, norbornyl, bicyclo[2.2.2]octyl.

Examples for unsaturated lower alkyl are vinyl, allyl, butenyl, pentenyl, pentadienyl, hexenyl, hexadienyl.

Examples for substituents in these radicals are hydroxy, methoxy, ethoxy, propoxy, isopropoxy, amino, monoalkylamino, dialkylamino, acylamino, halogen, acyl, carboxy, carbamido.

Examples for monoalkylamino are methylamino, ethylamino, n-propylamino, isopropylamino, n-butylamino, isobutylamino, sec-butylamino, tert-butylamino, 1-pentylamino, 2-pentylamino, 3-pentylamino, isopentylamino, tert-pentylamino, neopentylamino, hexylamino and its isomers.

Examples for dialkylamino are N,N-dimethylamino, N-methyl-N-ethylamino, N,N-diethylamino, N-propyl-N-methylamino, N-methyl-N-isopropylamino, dipropylamino, diisopropylamino, N-butyl-N-methylamino and its isomers, N-butyl-N-ethylamino and its isomers, N-butyl-N-propylamino and its isomers, N,N-dibutylamino and its isomers.

The alkyl groups of dialkylamino may also form a ring together. Examples are azetidine, pyrrolidine, piperidine, morpholine, piperazine, N'-alkylpiperazine, azabicylo[2.1.1]hexane, azanorbornane, azabicyclo[2.2.2]octane.

Examples for acyl are formyl, acetyl, propionyl, butyryl, pivaloyl, benzoyl, alkoxycarbonyl.

Examples for acylamino are N-formylamino, N-acetylamino, N-tert-butoxycarbonyl-amino, N-benzyloxycarbonyl-amino, N-benzoyl-amino, N-phthaloyl.

Examples for substituted aryl are tolyl, chlorphenyl, methoxyphenyl, aminophenyl, dimethylaminophenyl, 1-naphthyl, 2-naphthyl.

Examples for heteroaryl are thiazole, oxazole, imidazole, pyridine, pyrazole, pyrimidine, pyrazine, triazine, benzthiazole, benzoxazole, benzimidazole.

Examples of sulfonium groups are dimethylsulfonium, S-methyl-S-phenylsulfonium, S-methyl-S-allylsulfonium, S-methyl-S-carboxamidomethyl-sulfonium, S-dodecyl-S-methylsulfonium.

Examples for groups of the formula V are N-methyl-pyridinium-2-ylthio, N-methyl-pyridinium-4-ylthio, N-methyl-triazinylthio, N-methyl-benzthiazol-2-ylthio, pyridinium-2-ylthio toluenesulfonate, pyridinium-4-ylthio toluenesulfonate, pyridinium-2-ylthio methanesulfonate.

Compounds of the formula I in which C is a sarcosine substituted by S—R2 are prepared by forming polyanions from cyclosporins in which C is sarcosine and reacting these polyanions with appropriate sulfur electrophiles like disulfides, thiolsulfinates, sulfenyl halides, or disulfide-derived sulfonium salts. The polyanions are in turn prepared by treating the cyclosporins in an appropriate solvent at low temperature with an excess of a strong base. Examples for strong bases are alkali amides like lithium amide, natrium amide, lithium diisopropylamide or lithium hexamethyl disilazide. Examples for inert solvents used for these reactions are tetrahydrofurane, dioxane, diethylether, methyl tert-butylether, or liquid ammonia.

Compounds of the formula I in which C is sarcosine substituted by S—R2 are furthermore prepared by exchanging the substituent X in compounds of formula I in which C is sarcosine substituted by X and where X is a residue of formula IV or formula V by thiols HS—R2, in which R2 is lower alkyl, aryl, or acyl.

A compound of the formula I in which C is sarcosine substituted by S—R2 in which R2 is hydrogen is prepared by treating compounds of formula I in which C is sarcosine substituted by S—R2 and in which R2 is acyl in an appropriate solvent with ammonia, hydrazine, hydroxylamine, or organic derivatives thereof, such as methylamine, benzylamine, methylhydrazine, or dimethylhydrazine. Appropriate solvents for these reactions are alcohols, such as methanol or ethanol, ethers such as diethylether, tetrahydrofurane, or dioxane, or inert aprotic solvents, such as dimethyl formamide. The resulting thiol can be isolated but is more conveniently alkylated directly by adding to these reactions an alkylating agent such as an alkyl halide or esters of alcohols with sulfuric acid, or organic sulfonic acids such as 4-toluene sulfonic acid, methane sulfonic acid, or trifluoromethane sulfonic acid. The present invention makes it therefore possible to produce compounds of the formula I in which C is sarcosine substituted by S—R2 in which R2 is substituted or unsubstituted, branched or unbranched, saturated or unsaturated, acyclic, monocyclic, or polycyclic lower alkyl.

Compounds of the formula I in which C is a sarcosine substituted by SO—R2 and by SO2—R2 are prepared by treating compounds of formula I in which C is sarcosine substituted by S—R2 with an appropriate oxidant in an inert solvent. Examples for such oxidants are hydrogen peroxide, sodium chlorate, sodium periodate, peroxyacetic acid, meta-chloroperbenzoic acid, or potassium persulfate. Solvents for these reactions are for example mixtures of water with organic solvents such as tetrahydrofurane, dioxane or acetic acid, or anhydrous organic solvents such as dichloromethane, chloroform, tetrachloroethane, tetrahydrofurane, or dioxane.

Compounds of the formula I in which C is a sarcosine substituted by O—R3 can be prepared by exchanging the substituent S—R2 in compounds of formula I in which C is sarcosine substituted by S—R2. This exchange reaction is effected by metal salts which have an affinity for sulfur, such as mercuric acetate, silver acetate, copper acetate and others, but can also be effected by the presence of Bronsted or Lewis acids. The acidic nature of Bronsted acids is due to their capacity to act as proton donors. Such acids are for example sulfuric acid, toluene sulfonic or camphersulfonic acid, hydrochloric acid, but also acetic acid, formic acid and other organic carboxylic acids. Lewis acids are compounds having affinity for free electron pairs and forming coordination complexes with groups having free electron pairs. Examples for Lewis acids are boron trifluoride, titanium tetrachloride, aluminum chloride, or zinc chloride. Such Bronsted or Lewis acids or metal salts convert S—R2 or O—R'3 substituents at the sarcosine position of the cyclosporin macrocycle into leaving groups, forming an intermediary cation of the formula VI which can then further react with nucleophiles present in the reaction mixture to form the desired products.

The present invention makes it therefore also possible to exchange one given O—R3 substituent for another O—R3' substituent by using the reaction conditions as described above.

A compound of formula I in which the amino acid residue of C is the cation of Formula VII is a common intermediate for these exchange reactions. This type of cation is well known to experts in the field and is analogous to the commonly accepted intermediate in the Mannich reaction. In the case of cyclosporins, however, such an intermediate has never been described and is new. Mannich reactions are used to introduce aminoalkyl residues into a wide variety of nucleophiles, such as enols, phenols, enamines, heterocycles such as indole, pyrrol, or furane. Other nucleophiles reacting with such cations are allyl and vinylsilanes and -stannanes as well as acetylenes. Therefore, cyclosporins in which the amino acid residue of C is the cation of Formula VII are an especially preferred embodiment of the present invention.

The compounds of the present invention act on enzymes called cyclophilins and inhibit their catalytic activity. Cyclophilins occur in a wide variety of different organisms, including human, yeast, bacteria, protozoa, metazoa, insects, plants, or viruses. In the case of infectious organisms, inhibition of the cyclophilin catalytic activity by compounds of the present invention often results in an inhibitory effect on the organism. Furthermore, in humans the catalytic activity of cyclophilins plays a role in many different disease situations. Inhibition of this catalytic activity is often associated to a therapeutic effect. Therefore, the compounds of the present invention can be used for the treatment of infections including that by HIV as well as fungal pathogens, protozoan and metazoan parasites. Furthermore, the compounds of the present invention can be used to treat chronic inflammatory and autoimmune diseases including but not limited to rheumatoid arthritis, psoriasis, and uveitis. In addition, the compounds of the present invention can be used to treat neurodegenerative diseases such as Alzheimer's disease, Parkinson's disease, and neuropathies.

Another use of the compounds of the present invention is protection against tissue damage associated to ischemia and reperfusion such as paralytic damage after spinal cord or head injuries or cardiac damage after myocardial infarct.

Furthermore, the compounds of the present invention induce regenerative processes such as that of hair, liver, gingiva, or nerve tissue damaged or lost due to injury or other underlying pathologies, such as damage of the optical nerve in glaucoma.

The compounds of the present invention can, together with pharmaceutically acceptable additives and/or excipients be administered either orally in the form of capsules, tablets, or drink solutions or parenterally in form of acute injections or infusions. They can also be applied locally in form of solutions, eye drops, or as gels and ointments. For topical and parenteral applications it is of special advantage that, unlike cyclosporin A, many of the compounds of the present invention have basic substituents which enable the formation of salts with physiologically acceptable acids.

The daily administered dosage depends on the structure of the medicament, the disease to be treated, and the type of formulation and is from about 1 mg to about 200 mg per kg body weight.

The present invention will now be illustrated in more detail in the following Examples. It should be noted that the Examples are merely illustrative and that other embodiments are also possible and encompassed by the claims. Thus, the following Examples should not be construed to limit the spirit and scope of the claims.

EXAMPLES 1. 3-(Pyridyl-2-thio)-cyclosporin

Liquid ammonia (200 ml) is condensed in a flask under argon. Freshly cut sodium (1.78 g, 75 mmol) is added in 4 portions, followed by one crystal of ferric nitrate. The mixture is vigorously stirred for 15 minutes, at which time a dark grey color persists. A solution of cyclosporin A (5 g, 4 mmol) in tert.-butylmethyl ether (90 ml) is added over 15 minutes and the mixture is stirred at minus 40° Celsius for 1.5 hrs. Then, a solution of 2,2'-dipyridyl disulfide (7.2 g, 33 mmol) in 70 ml tert.-butylmethyl ether is added and stirring continued for 2 hrs at minus 35°–minus 40°. Solid ammonium chloride (5.56 g, 104 mmol) is added, stirring continued at minus 35° for 10 minutes. After warming to room temperature, the mixture is stirred for another 2 hrs, filtered, the residue washed 3 times with tert.-butylmethyl ether, and filtrate and washings combined, extracted with 2N sodium hydroxide, brine and dried over sodium sulfate. Chromatography of the residue obtained upon evaporation on silica, eluting with diethyl ether/methanol=96/4 yielded the title compound as two isomers.

The $^1$H-NMR chemical shift of the proton at the sarcosine residue [δ(H3)] for isomer A of the title compound is at 6.36 ppm, for isomer B at 7.13 ppm. The corresponding values in the $^{13}$C-NMR [δ(C3)] are 58.81 and 58.45 ppm.

Analogous to example 1, the following disulfides were used to prepare the following products:

| Example | Disulfide | Product |
|---|---|---|
| 2 | 4,4'-dipyridyldisulfide | 3-(Pyridyl-4-thio)-cyclosporin A |
| 3 | 2,2'-dipyridyldisulfide | 3-(Pyridyl-2-thio)-4-(γ-hydroxy-methylleucine)-cyclosporin |
| 4 | 2,2'-dipyridyldisulfide | 3-(Pyridyl-2-thio)-4-methylvaline-cyclosporin |
| 5 | 2,2'-dipyridyldisulfide | 3-(Pyridyl-2-thio)-2-norvaline-cyclosporin |
| 6 | 2,2'-dipyridyldisulfide | 3-(Pyridyl-2-thio)-2-valine-cyclosporin |
| 7 | 2,2'-dipyridyldisulfide | 3-(Pyridyl-2-thio)-8-(D)-serine-cyclosporin |
| 8 | diphenyldisulfide | 3-(Phenylthio)-cyclosporin A |
| 9 | 2,2'-dimethylaminoethyldisulfide | 3-(2-dimethylaminoethylthio)-cyclosporin |
| 10 | 2,2'-mercaptobenzthiazolyl-disulfide | 3-(Mercaptobenzthiazol-2-ylthio)-cyclosporin |

The products of these examples have the following physiochemical data:

| Example | Product | δ (H3) (CDCl3) | δ (C3) (CDCl3) | Calc Mass | High Resolution MS |
|---|---|---|---|---|---|
| 2 | 3-(Pyridyl-4-thio)-cyclosporin A | | | | |
| | isomer A | 6.36 | 60.19 | 1311.84 | 1311.8850 |
| | isomer B | 7.13 | 58.46 | | |
| 3 | 3-(Pyridyl-2-thio)-4-(γ-hydroxy-methylleucine)-cyclosporin | 7.12 | 58.58 | 1327.84 | 1327.7922 |
| 4 | 3-(Pyridyl-2-thio)-4-methylvaline-cyclosporin | 7.12 | 58.45 | 1297.83 | 1297.7507 |
| 5 | 3-(Pyridyl-2-thio)-2-norvaline-cyclosporin | 7.12 | 58.77 | 1325.86 | 1325.8316 |
| 6 | 3-(Pyridyl-2-thio)-2-valine-cyclosporin | | | | |
| | isomer A | 7.08 | 58.81 | 1325.86 | 1325.8517 |
| | isomer B | 7.33 | 58.45 | | |
| 7 | 3-(Pyridyl-2-thio)-8-(D)-serine-cyclosporin | | | | |
| | Isomer A | 7.11 | 58.12 | | |
| | Isomer B | 7.60 | 57.63 | 1327.84 | 1327.8436 |
| 8 | 3-(Phenylthio)-cyclosporin A | 6.18 | 63.62 | 1310.85 | 1310.8732 |
| 9 | 3-(2-dimethylaminoethylthio)-cyclosporin | 5.77 | 59.32 | 1305.89 | 1305.8762 |
| 10 | 3-(Mercpto-benzthiazol-2-ylthio)-cyclosporin, | | | | |
| | Isomer A | 7.0 | 63.00 | 1367.86 | 1366.8120 |
| | Isomer B | 7.56 | 60.90 | | |

11. 3'-Acetoxy-3-phenylthio-cyclosporin

To a stirred solution of 700 mg the product of example 8 and 300 mg of 4-dimethylamino pyridine in 3 ml pyridine was added 0.5 ml acetic anhydride. The solution was stirred at ambient temperature for 36 hrs and then diluted with 20 ml cold water. The mixture was extracted three times with ethyl acetate, the organic extracts were combined and washed successively with 1N sulfuric acid, water, brine and dried over sodium sulfate. The residue obtained from evaporation to dryness was chromatographed on silica gel using ethyl acetate as eluent. The title product was obtained as yellow foam.

12. 3',3-Diacetoxy-cyclosporin

The product of example 11 (100 mg) was dissolved in 2 ml acetic acid, mercuric acetate (100 mg) was added and the mixture was heated to 50° for 3 hrs. After evaporation to dryness the residue was taken up in ethyl acetate and washed with sodium bicarbonate solution. The organic phase was dried over sodium sulfate and evaporated to dryness. Chromatography of the residue on silica gel yielded 45 mg of the title compound. The characteristic NMR signals of this compound in deuterochloroform are at 6.80 ppm (sarcosine H) and 74.53 ppm (sarcosine C).

13. 3-Acetoxy-cyclosporin

To a stirred solution of 500 mg of the product of example 8 in 3 ml acetic acid was added silver acetate (100 mg) and the mixture was warmed to 50° for 20 hrs. After evaporation to dryness the residue was taken up in ethyl acetate and washed with sodium bicarbonate solution. The organic phase was dried over sodium sulfate and evaporated to dryness. Chromatography of the residue on silica gel yielded 45 mg of the title compound. The characteristic NMR signals of this compound in deuterochloroform are at 6.82 ppm (sarcosine H) and 74.40 ppm (sarcosine C).

14. 3-Methoxycyclosporin

The product of example 1 (131 mg) was dissolved in 2 ml methanol, camphersulfonic acid (25 mg) was added and the mixture heated to 50° for 5 hrs. After addition of aqueous ammonia (0.5 ml) and evaporation to dryness the residue was taken up in ethyl acetate and washed with sodium bicarbonate solution. The organic phase was dried over sodium sulfate and evaporated to dryness. Chromatography of the residue on silica gel yielded 45 mg of the title compound. The characteristic NMR signals of this compound in deuterochloroform are at 5.84 ppm (sarcosine H) and 83.30 ppm (sarcosine C).

This compound is also prepared under identical conditions using the product of example 12 as starting material in place of the product of example 1.

Analogous to example 14 the following alcohols were used to prepare the following products:

| Example | Alcohol | Product | δ(H3) (CDCl3) | δ(C3) (CDCl3) |
|---|---|---|---|---|
| 15 | Ethanol | 3-Ethoxycyclosporin | 5.93 | 81.58 |
| 16 | Isopropyl alcohol | 3-Isopropyloxycyclosporin | 6.02 | 79.50 |

17. [D-Sar-(tert.-butoxy)$^3$]-cyclosporin

Following the procedure of example 14 but using the product of example 10 instead of the product of example 1 and using tert.-butanol instead of methanol, the title compound is obtained. The characteristic NMR signals of this compound in deuterochloroform are at 6.09 ppm (sarcosine H) and 76.00 ppm (sarcosine C). The calculated mass is 1274.74, the mass determined by high resolution MS is 1273.898884.

18. [D-Sar-(allyloxy)³]-cyclosporin

Following the procedure of example 17 and using allyl alcohol in place of tert.-butanol, the title compound is obtained. The characteristic NMR signals of this compound in deuterochloroform are at 5.96 ppm (sarcosine H) and 80.80 ppm (sarcosine C). The calculated mass is 1258.69, the mass determined by high resolution MS is 1257.867583.

19. [D-Sar-(hydroxy)³]-cyclosporin

The product of example 1 (130 mg) was dissolved in 2 ml tetrahydrofurane, 1N sulfuric acid (1 ml) was added and the mixture heated to 50° for 5 hrs. After addition of aqueous ammonia (0.5 ml), ethyl acetate was added, the mixture was vigorously shaken and, after separation of the organic layer it was washed with sodium bicarbonate solution. The organic phase was dried over sodium sulfate and evaporated to dryness. Chromatography of the residue on silica gel yielded 55 mg of the title compound. The characteristic NMR signal of this compound in deuterochloroform is at 6.96 ppm (sarcosine H). The calculated mass is 1218.63, the mass determined by high resolution MS is 1217.836248.

20. [D-Sar-(acetylthio)³]-cyclosporin

The product of example 1 (500 mg) was dissolved in 2 ml tetrahydrofurane and 2 ml thioacetic acid. Camphersulfonic acid (200 mg) was added and the mixture heated to 50° for 5 hrs. After addition of aqueous ammonia (1 ml), ethyl acetate was added, the mixture was vigorously shaken and, after separation of the organic layer it was washed with sodium bicarbonate solution. The organic phase was dried over sodium sulfate and evaporated to dryness. Chromatography of the residue on silica gel yielded 255 mg of the title compound. The characteristic NMR signals of this compound in deuterochloroform are at 6.50 ppm (sarcosine H) and 57.60 ppm (sarcosine C). The calculated mass is 1276.73, the mass determined by high resolution MS is 1276.824005.

21. [D-Sar-(methylthio)³]-cyclosporin

Under argon atmosphere, the product of example 19 (120 mg) was dissolved in 1 ml ethanol. N,N-dimethylhydrazine (60 mg) was added and the mixture stirred at room temperature for 5 hrs. After addition of methyl iodide (0.5 ml) stirring was continued over night. The mixture was concentrated to dryness and the residue partitioned between ethyl acetate and 1N sulfuric acid. The organic layer was washed with sodium bicarbonate solution and brine, dried over anhydrous sodium sulfate and evaporated to dryness. Chromatography of the residue on silica gel yielded 75 mg of the title compound. The compound has the following optical rotation: $[\alpha]^{20}_D = -215°$, c=1, CHCl3. A value of $[\alpha]^{20}_D = -215°$, c=1, CHCl3, has been reported for this compound.

22. [D-Sar-(2-(N-Boc-3-aminopropoxy))³]-cyclosporin

The product of example 10 (140 mg) was dissolved in 5 ml dry tetrahydrofurane, 175 mg N-Boc-3-aminopropanol and Camphersulfonic acid (30 mg) were added and the mixture heated to 50° for 12 hrs. The mixture was evaporated to dryness, the residue taken up in ethyl acetate and saturated sodium bicarbonate solution. The layers were separated, the organic phase was dried over sodium sulfate and evaporated to dryness. Repeated chromatography of the residue on silica gel yielded 75 mg of the title compound and 23 mg [D-Sar-(2-(3-aminopropoxy))³]-cyclosporin. The characteristic NMR signal of the title compound in deuterochloroform is at 5.97 ppm (sarcosine H), that of [D-Sar-(2-(3-aminopropoxy))³]-cyclosporin at 5.91 ppm.

According to the procedure described in example 22 and using the following the following products are obtained:

| Example | Alcohol | Product |
|---|---|---|
| 23 | N-Boc-2-aminoethanol | [D-Sar-(2-(N-Boc-3-aminoethoxy))³]-cyclosporin |
| 24 | | [D-Sar-(2-(3-aminoethoxy))³]-cyclosporin |
| 25 | N-Boc-5-aminopentanol | [D-Sar-(2-(N-Boc-3-aminopentoxy))³]-cyclosporin |
| 26 | | [D-Sar-(2-(3-aminopentoxy))³]-cyclosporin |
| 27 | N,N-dimethyl-aminoethanol | [D-Sar-(2-(N,N-dimethylaminoethoxy))³]-cyclosporin |
| 28 | N,N-diethylaminoethanol | [D-Sar-(2-(N,N-diethylaminoethoxy))³]-cyclosporin |
| 29 | N-methyl-N-(1,1-dimethyl-ethyl)-aminoethanol | [D-Sar-(2-(N-methyl-N-(1,1-dimethyl-ethyl)-2-aminoethoxy))³]-cyclosporin |
| 30 | N-phthaloyl-aminoethanol | [D-Sar-(2-(N-phthalimido-2-aminoethoxy))³]-cyclosporin |
| 31 | N-Boc-2-amino-3-phenylpropanol | [D-Sar-(2-(N-Boc-2-amino-3-phenyl-propoxy))³]-cyclosporin |
| 32 | N-Boc-2-hydroxymethyl-pyrolidine | [D-Sar-(2-(N-Boc-pyrrolidine-2-yl)-methoxy)³]-cyclosporin |
| 33 | | [D-Sar-(2-(pyrrolidine-2-yl)-methoxy)³]-cyclosporin |
| 34 | N-methyl-4-hydroxypiperidine | [D-Sar-(2-(N-methyl-piperidine-4-yl)-oxy)³]-cyclosporin |
| 35 | N-methyl-3-hydroxyazetidine | [D-Sar-(2-(N-methyl-azetidine-3-yl)-oxy)³]-cyclosporin |

The characteristic NMR signals of these compounds are as follows:

| Example | Product | δ(H3) (CDCl3) | δ(C3) (CDCl3) |
|---|---|---|---|
| 23 | [D-Sar-(2-(N-Boc-3-aminoethoxy))³]-cyclosporin | 5.96 | 82.01 |
| 24 | [D-Sar-(2-(3-aminoethoxy))³]-cyclosporin | 5.92 | 81.53 |
| 25 | [D-Sar-(2-(N-Boc-3-aminopentoxy))³]-cyclosporin | 5.95 | 81.76 |
| 26 | [D-Sar-(2-(3-aminopentoxy))³]-cyclosporin | 5.94 | 81.73 |
| 27 | [D-Sar-(2-(N,N-dimethylaminoethoxy))³]-cyclosporin | 5.89 | 80.63 |
| 28 | [D-Sar-(2-(N,N-diethylaminoethoxy))³]-cyclosporin | 5.88 | 80.54 |
| 29 | [D-Sar-(2-(N-methyl-N-(1,1-dimethyl-ethyl)-2-aminoethoxy))³]-cyclosporin | 5.84 | 80.13 |
| 30 | [D-Sar-(2-(N-phthalimido-2-aminoethoxy))³]-cyclosporin | 5.99 | 82.12 |
| 31 | [D-Sar-(2-(N-Boc-2-amino-3-phenyl-propoxy))³]-cyclosporin | 5.96 | 81.89 |
| 32 | [D-Sar-(2-(N-Boc-pyrrolidine-2-yl)-methoxy)³]-cyclosporin | 5.87 | 79.46 |
| 33 | [D-Sar-(2-(pyrrolidine-2-yl)-methoxy)³]-cyclosporin | 5.85 | 79.32 |
| 34 | [D-Sar-(2-(N-methyl-piperidine-4-yl)-oxy)³]-cyclosporin | 5.85 | 79.32 |
| 35 | [D-Sar-(2-(N-methyl-azetidine-3-yl)-oxy)³]-cyclosporin | 6.03 | 78.50 |

Using the conditions of example 1 the following compounds can be obtained:

3-(2-Hydroxyethyl)thio-cyclosporin
3-(2-Hydroxypropyl)thio-cyclosporin
3-(2-Aminoethyl)thio-cyclosporin
3-(2-Methylaminoethyl)thio-cyclosporin
3-(2-Ethylaminoethyl)thio-cyclosporin
3-(2-Ethyl-N-methylaminoethyl)thio-cyclosporin
3-(2-Diethylaminoethyl)thio-cyclosporin
3-(2-n-Propylaminoethyl)thio-cyclosporin
3-(2-Isopropylaminoethyl)thio-cyclosporin
3-(2-Cyclopropylaminoethyl)thio-cyclosporin
3-(2-n-Propyl-methylaminoethyl)thio-cyclosporin
3-(2-n-Propyl-ethylaminoethyl)thio-cyclosporin
3-(2-Methyl-isopropylaminoethyl)thio-cyclosporin
3-(2-Methylcyclopropylaminoethyl)thio-cyclosporin
3-(2-Ethyl-isopropylaminoethyl)thio-cyclosporin
3-(2-Diisopropylaminoethyl)thio-cyclosporin
3-(2-n-Propyl-isopropylaminoethyl)thio-cyclosporin
3-(2-n-Butylaminoethyl)thio-cyclosporin
3-(2-sec-Butylaminoethyl)thio-cyclosporin
3-(2-Isobutylaminoethyl)thio-cyclosporin
3-(2-tert-Butylaminoethyl)thio-cyclosporin
3-(2-n-Butyl-methylaminoethyl)thio-cyclosporin
3-(2-n-Butyl-ethylaminoethyl)thio-cyclosporin
3-(2-n-Butyl-isopropylaminoethyl)thio-cyclosporin
3-(2-sec-Butyl-methylaminoethyl)thio-cyclosporin
3-(2-sec-Butyl-ethylaminoethyl)thio-cyclosporin
3-(2-sec-Butyl-isopropylaminoethyl)thio-cyclosporin
3-(2-tert-Butyl-methylaminoethyl)thio-cyclosporin
3-(2-tert-Butyl-ethylaminoethyl)thio-cyclosporin
3-(2-tert-Butyl-isopropylaminoethyl)thio-cyclosporin
3-(2-Azetidinoethyl)thio-cyclosporin
3-(2-pyrrolidinoethyl)thio-cyclosporin
3-(2-piperidinoethyl)thio-cyclosporin
3-(2-morpholinoethyl)thio-cyclosporin
3-(2-piperazinoethyl)thio-cyclosporin
3-(2-N-methylpiperazinoethyl)thio-cyclosporin
3-(2-N-tert-butylpiperazinoethyl)thio-cyclosporin
3-(3-azetidinyl)thio-cyclosporin
3-(N-methyl-3-azetidinyl)thio-cyclosporin
3-(N-methyl-3-azetidinyl)thio-cyclosporin
3-(N-isopropyl-3-azetidinyl)thiocyclosporin
3-(3-pyrrolidinyl)thio-cyclosporin
3-(N-methyl-3-pyrrolidinyl)thio-cyclosporin
3-(N-methyl-3-pyrrolidinyl)thio-cyclosporin
3-(N-isopropyl-3-pyrrolidinyl)thio-cyclosporin
3-(4-piperidinyl)thio-cyclosporin
3-(N-methyl-4-piperidinyl)thio-cyclosporin
3-(N-methyl-4-piperidinyl)thio-cyclosporin
3-(N-isopropyl-4-piperidinyl)thio-cyclosporin
3-(2-Hydroxyethyl)thio-2-valine-cyclosporin
3-(3-Hydroxypropyl)thio-2-valine-cyclosporin
3-(2-Aminoethyl)thio-2-valine-cyclosporin
3-(2-Methylaminoethyl)thio-2-valine-cyclosporin
3-(2-Ethylaminoethyl)thio-2-valine-cyclosporin
3-(2-Ethyl-N-methylaminoethyl)thio-2-valine-cyclosporin
3-(2-Diethylaminoethyl)thio-2-valine-cyclosporin
3-(2-n-Propylaminoethyl)thio-2-valine-cyclosporin
3-(2-Isopropylaminoethyl)thio-2-valine-cyclosporin
3-(2-Cyclopropylaminoethyl)thio-2-valine-cyclosporin
3-(2-n-Propyl-methylaminoethyl)thio-2-valine-cyclosporin
3-(2-n-Propyl-ethylaminoethyl)thio-2-valine-cyclosporin
3-(2-Methyl-isopropylaminoethyl)thio-2-valine-cyclosporin
3-(2-Methylcyclopropylaminoethyl)thio-2-valine-cyclosporin
3-(2-Ethyl-isopropylaminoethyl)thio-2-valine-cyclosporin
3-(2-Diisopropylaminoethyl)thio-2-valine-cyclosporin
3-(2-n-Propyl-isopropylaminoethyl)thio-2-valine-cyclosporin
3-(2-n-Butylaminoethyl)thio-2-valine-cyclosporin
3-(2-sec-Butylaminoethyl)thio-2-valine-cyclosporin
3-(2-Isobutylaminoethyl)thio-2-valine-cyclosporin
3-(2-tert-Butylaminoethyl)thio-2-valine-cyclosporin
3-(2-n-Butyl-methylaminoethyl)thio-2-valine-cyclosporin
3-(2-n-Butyl-ethylaminoethyl)thio-2-valine-cyclosporin
3-(2-n-Butyl-isopropylaminoethyl)thio-2-valine-cyclosporin
3-(2-sec-Butyl-methylaminoethyl)thio-2-valine-cyclosporin
3-(2-sec-Butyl-ethylaminoethyl)thio-2-valine-cyclosporin
3-(2-sec-Butyl-isopropylaminoethyl)thio-2-valine-cyclosporin
3-(2-tert-Butyl-methylaminoethyl)thio-2-valine-cyclosporin
3-(2-tert-Butyl-ethylaminoethyl)thio-2-valine-cyclosporin
3-(2-tert-Butyl-isopropylaminoethyl)thio-2-valine-cyclosporin
3-(2-Azetidinoethyl)thio-2-valine-cyclosporin
3-(2-pyrrolidinoethyl)thio-2-valine-cyclosporin
3-(2-piperidinoethyl)thio-2-valine-cyclosporin
3-(2-morpholinoethyl)thio-2-valine-cyclosporin
3-(2-piperazinoethyl)thio-2-valine-cyclosporin
3-(2-N-methylpiperazinoethyl)thio-2-valine-cyclosporin
3-(2-N-tert-butylpiperazinoethyl)thio-2-valine-cyclosporin
3-(3-azetidinyl)thio-2-valine-cyclosporin
3-(N-methyl-3-azetidinyl)thio-2-valine-cyclosporin
3-(N-methyl-3-azetidinyl)thio-2-valine-cyclosporin
3-(N-isopropyl-3-azetidinyl)thio-2-valine-cyclosporin
3-(3-pyrrolidinyl)thio-2-valine-cyclosporin
3-(N-methyl-3-pyrrolidinyl)thio-2-valine-cyclosporin
3-(N-methyl-3-pyrrolidinyl)thio-2-valine-cyclosporin
3-(N-isopropyl-3-pyrrolidinyl)thio-2-valine-cyclosporin
3-(4-piperidinyl)thio-2-valine-cyclosporin
3-(N-methyl-4-piperidinyl)thio-2-valine-cyclosporin
3-(N-methyl-4-piperidinyl)thio-2-valine-cyclosporin
3-(N-isopropyl-4-piperidinyl)thio-2-valine-cyclosporin
3-(2-Hydroxyethyl)thio-4-(gamma-hydroxy-methylleucine)-cyclosporin
3-(3-Hydroxypropyl)thio-4-(gamma-hydroxy-methylleucine)-cyclosporin
3-(2-Aminoethyl)thio-4-(gamma-hydroxy-methylleucine)-cyclosporin
3-(2-Methylaminoethyl)thio-4-(gamma-hydroxy-methylleucine)-cyclosporin
3-(2-Ethylaminoethyl)thio-4-(gamma-hydroxy-methylleucine)-cyclosporin
3-(2-Ethyl-N-methylaminoethyl)thio-4-(gamma-hydroxy-methylleucine)-cyclosporin
3-(2-Diethylaminoethyl)thio-4-(gamma-hydroxy-methylleucine)-cyclosporin
3-(2-n-Propylaminoethyl)thio-4-(gamma-hydroxy-methylleucine)-cyclosporin
3-(2-Isopropylaminoethyl)thio-4-(gamma-hydroxy-methylleucine)-cyclosporin
3-(2-Cyclopropylaminoethyl)thio-4-(gamma-hydroxy-methylleucine)-cyclosporin
3-(2-n-Propyl-methylaminoethyl)thio-4-(gamma-hydroxy-methylleucine)-cyclosporin
3-(2-n-Propyl-ethylaminoethyl)thio-4-(gamma-hydroxy-methylleucine)-cyclosporin
3-(2-Methyl-isopropylaminoethyl)thio-4-(gamma-hydroxy-methylleucine)-cyclosporin
3-(2-Methylcyclopropylaminoethyl)thio-4-(gamma-hydroxy-methylleucine)-cyclosporin
3-(2-Ethyl-isopropylaminoethyl)thio-4-(gamma-hydroxy-methylleucine)-cyclosporin 3-(2-Diisopropylaminoethyl)thio-4-(gamma-hydroxy-methylleucine)-cyclosporin
3-(2-n-Propyl-isopropylaminoethyl)thio-4-(gamma-hydroxy-methylleucine)-cyclosporin
3-(2-n-Butylaminoethyl)thio-4-(gamma-hydroxy-methylleucine)-cyclosporin
3-(2-sec-Butylaminoethyl)thio-4-(gamma-hydroxy-methylleucine)-cyclosporin
3-(2-Isobutylaminoethyl)thio-4-(gamma-hydroxy-methylleucine)-cyclosporin
3-(2-tert-Butylaminoethyl)thio-4-(gamma-hydroxy-methylleucine)-cyclosporin
3-(2-n-Butyl-methylaminoethyl)thio-4-(gamma-hydroxy-methylleucine)-cyclosporin
3-(2-n-Butyl-ethylaminoethyl)thio-4-(gamma-hydroxy-methylleucine)-cyclosporin
3-(2-n-Butyl-isopropylaminoethyl)thio-4-(gamma-hydroxy-methylleucine)-cyclosporin
3-(2-sec-Butyl-methylaminoethyl)thio-4-(gamma-hydroxy-methylleucine)-cyclosporin
3-(2-sec-Butyl-ethylaminoethyl)thio-4-(gamma-hydroxy-methylleucine)-cyclosporin
3-(2-sec-Butyl-isopropylaminoethyl)thio-4-(gamma-hydroxy-methylleucine)-cyclosporin
3-(2-tert-Butyl-methylaminoethyl)thio-4-(gamma-hydroxy-methylleucine)-cyclosporin
3-(2-tert-Butyl-ethylaminoethyl)thio-4-(gamma-hydroxy-methylleucine)-cyclosporin
3-(2-tert-Butyl-isopropylaminoethyl)thio-4-(gamma-hydroxy-methylleucine)-cyclosporin
3-(2-Azetidinoethyl)thio-4-(gamma-hydroxy-methylleucine)-cyclosporin
3-(2-pyrrolidinoethyl)thio-4-(gamma-hydroxy-methylleucine)-cyclosporin
3-(2-piperidinoethyl)thio-4-(gamma-hydroxy-methylleucine)-cyclosporin
3-(2-morpholinoethyl)thio-4-(gamma-hydroxy-methylleucine)-cyclosporin
3-(2-piperazinoethyl)thio-4-(gamma-hydroxymethylleucine)-cyclosporin
3-(2-N-methylpiperazinoethyl)thio-4-(gamma-hydroxy-methylleucine)-cyclosporin
3-(2-N-tert-butylpiperazinoethyl)thio-4-(gamma-hydroxy-methylleucine)-cyclosporin
3-(3-azetidinyl)thio-4-(gamma-hydroxy-methylleucine)-cyclosporin
3-(N-methyl-3-azetidinyl)thio-4-(gamma-hydroxy-methylleucine)-cyclosporin
3-(N-methyl-3-azetidinyl)thio-4-(gamma-hydroxy-methylleucine)-cyclosporin
3-(N-isopropyl-3-azetidinyl)thio-4gamma-hydroxy-methylleucine)-cyclosporin
3-(3-pyrrolidinyl)thio-4-(gamma-hydroxy-methylleucine)-cyclosporin
3-(N-methyl-3-pyrrolidinyl)thio-4-(gamma-hydroxy-methylleucine)-cyclosporin
3-(N-methyl-3-pyrrolidinyl)thio-4-(gamma-hydroxy-methylleucine)-cyclosporin
3-(N-isopropyl-3-pyrrolidinyl)thio-4-(gamma-hydroxy-methylleucine)-cyclosporin
3-(4-piperidinyl)thio-4-(gamma-hydroxy-methylleucine)-cyclosporin
3-(N-methyl-4-piperidinyl)thio-4-(gamma-hydroxy-methylleucine)-cyclosporin
3-(N-methyl-4-piperidinyl)thio-4-(gamma-hydroxy-methylleucine)-cyclosporin
3-(N-isopropyl-4-piperidinyl)thio-4-(gamma-hydroxy-methylleucine)-cyclosporin
3-(2-Hydroxyethyl)thio-2-norvaline-cyclosporin
3-(3-Hydroxypropyl)thio-2-norvaline-cyclosporin
3-(2-Aminoethyl)thio-2-norvaline-cyclosporin
3-(2-Methylaminoethyl)thio-2-norvaline-cyclosporin
3-(2-Ethylaminoethyl)thio-2-norvaline-cyclosporin
3-(2-Ethyl-N-methylaminoethyl)thio-2-norvaline-cyclosporin
3-(2-Diethylaminoethyl)thio-2-norvaline-cyclosporin
3-(2-n-Propylaminoethyl)thio-2-norvaline-cyclosporin
3-(2Isopropylaminoethyl)thio-2-norvaline-cyclosporin
3-(2-Cyclopropylaminoethyl)thio-2-norvaline-cyclosporin
3-(2-n-Propyl-methylaminoethyl)thio-2-norvaline-cyclosporin
3-(2-n-Propyl-ethylaminoethyl)thio-2-norvaline-cyclosporin
3-(2-Methyl-isopropylaminoethyl)thio-2-norvaline-cyclosporin
3-(2-Methylcyclopropylaminoethyl)thio-2-norvaline-cyclosporin
3-(2-Ethyl-isopropylaminoethyl)thio-2-norvaline-cyclosporin
3-(2-Diisopropylaminoethyl)thio-2-norvaline-cyclosporin
3-(2-n-Propyl-isopropylaminoethyl)thio-2-norvaline-cyclosporin
3-(2-n-Butylaminoethyl)thio-2-norvaline-cyclosporin
3-(2-sec-Butylaminoethyl)thio-2-norvaline-cyclosporin
3-(2Isobutylaminoethyl)thio-2-norvaline-cyclosporin
3-(2-tert-Butylaminoethyl)thio-2-norvaline-cyclosporin
3-(2-n-Butyl-methylaminoethyl)thio-2-norvaline-cyclosporin
3-(2-n-Butyl-ethylaminoethyl)thio-2-norvaline-cyclosporin
3-(2-n-Butyl-isopropylaminoethyl)thio-2-norvaline-cyclosporin
3-(2-sec-Butyl-methylaminoethyl)thio-2-norvaline-cyclosporin
3-(2-sec-Butyl-ethylaminoethyl)thio-2-norvaline-cyclosporin
3-(2-sec-Butyl-isopropylaminoethyl)thio-2-norvaline-cyclosporin
3-(2-tert-Butyl-methylaminoethyl)thio-2-norvaline-cyclosporin
3-(2-tert-Butyl-ethylaminoethyl)thio-2-norvaline-cyclosporin
3-(2-tert-Butyl-isopropylaminoethyl)thio-2-norvaline-cyclosporin
3-(2-Azetidinoethyl)thio-2-norvaline-cyclosporin
3-(2-pyrrolidinoethyl)thio-2-norvaline-cyclosporin
3-(2-piperidinoethyl)thio-2-norvaline-cyclosporin
3-(2-morpholinoethyl)thio-2-norvaline-cyclosporin
3-(2-piperazinoethyl)thio-2-norvaline-cyclosporin
3-(2-N-methylpiperazinoethyl)thio-2-norvaline-cyclosporin
3-(2-N-tert-butylpiperazinoethyl)thio-2-norvaline-cyclosporin
3-(3-azetidinyl)thio-2-norvaline-cyclosporin
3-(N-methyl-3-azetidinyl)thio-2-norvaline-cyclosporin
3-(N-methyl-3-azetidinyl)thio-2-norvaline-cyclosporin
3-(N-isopropyl-3-azetidinyl)thio-2-norvaline-cyclosporin
3-(3-pyrrolidinyl)thio-2-norvaline-cyclosporin
3-(N-methyl-3-pyrrolidinyl)thio-2-norvaline-cyclosporin
3-(N-methyl-3-pyrrolidinyl)thio-2-norvaline-cyclosporin
3-(N-isopropyl-3-pyrrolidinyl)thio-2-norvaline-cyclosporin
3-(4-piperidinyl)thio-2-norvaline-cyclosporin
3-(N-methyl-4-piperidinyl)thio-2-norvaline-cyclosporin
3-(N-methyl-4-piperidinyl)thio-2-norvaline-cyclosporin
3-(N-isopropyl-4-piperidinyl)thio-2-norvaline-cyclosporin
3-(2-Hydroxyethyl)thio-4-methylvaline-cyclosporin
3-(3-Hydroxypropyl)thio-4-methylvaline-cyclosporin 3-(2-Aminoethyl)thio-4-methylvaline-cyclosporin
3-(2-Methylaminoethyl)thio-4-methylvaline-cyclosporin
3-(2-Ethylaminoethyl)thio-4-methylvaline-cyclosporin
3-(2-Ethyl-N-methylaminoethyl)thio-4-methylvaline-cyclosporin
3-(2-Diethylaminoethyl)thio-4-methylvaline-cyclosporin
3-(2-n-Propylaminoethyl)thio-4-methylvaline-cyclosporin
3-(2Isopropylaminoethyl)thio-4-methylvaline-cyclosporin
3-(2-Cyclopropylaminoethyl)thio-4-methylvaline-cyclosporin
3-(2-n-Propyl-methylaminoethyl)thio-4-methylvaline-cyclosporin
3-(2-n-Propyl-ethylaminoethyl)thio-4-methylvaline-cyclosporin
3-(2-Methyl-isopropylaminoethyl)thio-4-methylvaline-cyclosporin
3-(2-Methylcyclopropylaminoethyl)thio-4-methylvaline-cyclosporin
3-(2-Ethyl-isopropylaminoethyl)thio-4-methylvaline-cyclosporin
3-(2-Diisopropylaminoethyl)thio-4-methylvaline-cyclosporin
3-(2-n-Propyl-isopropylaminoethyl)thio-4-methylvaline-cyclosporin
3-(2-n-Butylaminoethyl)thio-4-methylvaline-cyclosporin
3-(2-sec-Butylaminoethyl)thio-4-methylvaline-cyclosporin
3-(2-Isobutylaminoethyl)thio-4-methylvaline-cyclosporin
3-(2-tert-Butylaminoethyl)thio-4-methylvaline-cyclosporin
3-(2-n-Butyl-methylaminoethyl)thio-4-methylvaline-cyclosporin
3-(2-n-Butyl-ethylaminoethyl)thio-4-methylvaline-cyclosporin
3-(2-n-Butyl-isopropylaminoethyl)thio-4-methylvaline-cyclosporin
3-(2-sec-Butyl-methylaminoethyl)thio-4-methylvaline-cyclosporin
3-(2-sec-Butyl-ethylaminoethyl)thio-4-methylvaline-cyclosporin
3-(2-sec-Butyl-isopropylaminoethyl)thio-4-methylvaline-cyclosporin
3-(2-tert-Butyl-methylaminoethyl)thio-4-methylvaline-cyclosporin
3-(2-tert-Butyl-ethylaminoethyl)thio-4-methylvaline-cyclosporin
3-(2-tert-Butyl-isopropylaminoethyl)thio-4-methylvaline-cyclosporin
3-(2-Azetidinoethyl)thio-4-methylvaline-cyclosporin
3-(2-pyrrolidinoethyl)thio-4-methylvaline-cyclosporin
3-(2-piperidinoethyl)thio-4-methylvaline-cyclosporin
3-(2-morpholinoethyl)thio-4-methylvaline-cyclosporin
3-(2-piperazinoethyl)thio-4-methylvaline-cyclosporin
3-(2-N-methylpiperazinoethyl)thio-4-methylvaline-cyclosporin
3-(2-N-tert-butylpiperazinoethyl)thio-4-methylvaline-cyclosporin
3-(3-azetidinyl)thio-4-methylvaline-cyclosporin
3-(N-methyl-3-azetidinyl)thio-4-methylvaline-cyclosporin
3-(N-methyl-3-azetidinyl)thio-4-methylvaline-cyclosporin
3-(N-isopropyl-3-azetidinyl)thio-4-methylvaline-cyclosporin
3-(3-pyrrolidinyl)thio-4-methylvaline-cyclosporin
3-(N-methyl-3-pyrrolidinyl)thio-4-methylvaline-cyclosporin
3-(N-methyl-3-pyrrolidinyl)thio-4-methylvaline-cyclosporin
3-(N-isopropyl-3-pyrrolidinyl)thio-4-methylvaline-cyclosporin
3-(4-piperidinyl)thio-4-methylvaline-cyclosporin
3-(N-methyl-4-piperidinyl)thio-4-methylvaline-cyclosporin
3-(N-methyl-4-piperidinyl)thio-4-methylvaline-cyclosporin
3-(N-isopropyl-4-piperidinyl)thio-4-methylvaline-cyclosporin
3-(2-Hydroxyethyl)thio-4-methylisoleucine-cyclosporin
3-(3-Hydroxypropyl)thio-4-methylisoleucine-cyclosporin
3-(2-Aminoethyl)thio-4-methylisoleucine-cyclosporin
3-(2-Methylaminoethyl)thio-4-methylisoleucine-cyclosporin
3-(2-Ethylaminoethyl)thio-4-methylisoleucine-cyclosporin
3-(2-Ethyl-N-methylaminoethyl)thio-4-methylisoleucine-cyclosporin
3-(2-Diethylaminoethyl)thio-4-methylisoleucine-cyclosporin
3-(2-n-Propylaminoethyl)thio-4-methylisoleucine-cyclosporin
3-(2-Isopropylaminoethyl)thio-4-methylisoleucine-cyclosporin
3-(2-Cyclopropylaminoethyl)thio-4-methylisoleucine-cyclosporin
3-(2-n-Propyl-methylaminoethyl)thio-4-methylisoleucine-cyclosporin
3-(2-n-Propyl-ethylaminoethyl)thio-4-methylisoleucine-cyclosporin
3-(2-Methyl-isopropylaminoethyl)thio-4-methylisoleucine-cyclosporin
3-(2-Methylcyclopropylaminoethyl)thio-4-methylisoleucine-cyclosporin
3-(2-Ethyl-isopropylaminoethyl)thio-4-methylisoleucine-cyclosporin
3-(2-Diisopropylaminoethyl)thio-4-methylisoleucine-cyclosporin
3-(2-n-Propyl-isopropylaminoethyl)thio-4-methylisoleucine-cyclosporin
3-(2-n-Butylaminoethyl)thio-4-methylisoleucine-cyclosporin
3-(2-sec-Butylaminoethyl)thio-4-methylisoleucine-cyclosporin
3-(2-Isobutylaminoethyl)thio-4-methylisoleucine-cyclosporin
3-(2-tert-Butylaminoethyl)thio-4-methylisoleucine-cyclosporin
3-(2-n-Butyl-methylaminoethyl)thio-4-methylisoleucine-cyclosporin
3-(2-n-Butyl-ethylaminoethyl)thio-4-methylisoleucine-cyclosporin
3-(2-n-Butyl-isopropylaminoethyl)thio-4-methylisoleucine-cyclosporin
3-(2-sec-Butyl-methylaminoethyl)thio-4-methylisoleucine-cyclosporin
3-(2-sec-Butyl-ethylaminoethyl)thio-4-methylisoleucine-cyclosporin
3-(2-sec-Butyl-isopropylaminoethyl)thio-4-methylisoleucine-cyclosporin
3-(2-tert-Butyl-methylaminoethyl)thio-4-methylisoleucine-cyclosporin
3-(2-tert-Butyl-ethylaminoethyl)thio-4-methylisoleucine-cyclosporin
3-(2-tert-Butyl-isopropylaminoethyl)thio-4-methylisoleucine-cyclosporin
3-(2-Azetidinoethyl)thio-4-methylisoleucine-cyclosporin
3-(2-pyrrolidinoethyl)thio-4-methylisoleucine-cyclosporin
3-(2-piperidinoethyl)thio-4-methylisoleucine-cyclosporin
3-(2-morpholinoethyl)thio-4methylisoleucine-cyclosporin
3-(2-piperazinoethyl)thio-4-methylisoleucine-cyclosporin
3-(2-N-methylpiperazinoethyl)thio-4-methylisoleucine-cyclosporin 3-(2-N-tert-butylpiperazinoethyl)thio-4-methylisoleucine-cyclosporin
3-(3-azetidinyl)thio-4-methylisoleucine-cyclosporin
3-(N-methyl-3-azetidinyl)thio-4-methylisoleucine-cyclosporin
3-(N-methyl-3-azetidinyl)thio-4-methylisoleucine-cyclosporin
3-(N-isopropyl-3-azetidinyl)thio-4-methylisoleucine-cyclosporin
3-(3-pyrrolidinyl)thio-4-methylisoleucine-cyclosporin
3-(N-methyl-3-pyrrolidinyl)thio-4-methylisoleucine-cyclosporin
3-(N-methyl-3-pyrrolidinyl)thio-4-methylisoleucine-cyclosporin
3-(N-isopropyl-3-pyrrolidinyl)thio-4-methylisoleucine-cyclosporin
3-(4-piperidinyl)thio-4-methylisoleucine-cyclosporin
3-(N-methyl-4-piperidinyl)thio-methylisoleucine-cyclosporin
3-(N-methyl-4-piperidinyl)thio-4-methylisoleucine-cyclosporin
3-(N-isopropyl-4-piperidinyl)thio-4-methylisoleucine-cyclosporin
3-(2-Hydroxyethyl)thio-8-(D)-serine-cyclosporin
3-(3-Hydroxypropyl)thio-8-(D)-serine-cyclosporin
3-(2-Aminoethyl)thio-8-(D)-serine-cyclosporin
3-(2-Methylaminoethyl)thio-8-(D)-serine-cyclosporin
3-(2-Ethylaminoethyl)thio-8-(D)-serine-cyclosporin
3-(2-Ethyl-N-methylaminoethyl)thio-8-(D)-serine-cyclosporin
3-(2-Diethylaminoethyl)thio-8-(D)-serine-cyclosporin
3-(2-n-Propylaminoethyl)thio-8-(D)-serine-cyclosporin
3-(2-Isopropylaminoethyl)thio-8-(D)-serine-cyclosporin
3-(2-Cyclopropylaminoethyl)thio-8-(D)-serine-cyclosporin
3-(2-n-Propyl-methylaminoethyl)thio-8-(D)-serine-cyclosporin
3-(2-n-Propyl-ethylaminoethyl)thio-8-(D)-serine-cyclosporin
3-(2-Methyl-isopropylaminoethyl)thio-8-(D)-serine-cyclosporin
3-(2-Methylcyclopropylaminoethyl)thio-8-(D)-serine-cyclosporin
3-(2-Ethyl-isopropylaminoethyl)thio-8-(D)-serine-cyclosporin
3-(2-Diisopropylaminoethyl)thio-8-(D)-serine-cyclosporin
3-(2-n-Propyl-isopropylaminoethyl)thio-8-(D)-serine-cyclosporin
3-(2-n-Butylaminoethyl)thio-8-(D)-serine-cyclosporin
3-(2-sec-Butylaminoethyl)thio-8-(D)-serine-cyclosporin
3-(2-Isobutylaminoethyl)thio-8-(D)-serine-cyclosporin
3-(2-tert-Butylaminoethyl)thio-8-(D)-serine-cyclosporin
3-(2-n-Butyl-methylaminoethyl)thio-8-(D)-serine-cyclosporin
3-(2-n-Butyl-ethylaminoethyl)thio-8-(D)-serine-cyclosporin
3-(2-n-Butyl-isopropylaminoethyl)thio-8-(D)-serine-cyclosporin
3-(2-sec-Butyl-methylaminoethyl)thio-8-(D)-serine-cyclosporin
3-(2-sec-Butyl-ethylaminoethyl)thio-8-(D)-serine-cyclosporin
3-(2-sec-Butyl-isopropylaminoethyl)thio-8-(D)-serine-cyclosporin
3-(2-tert-Butyl-methylaminoethyl)thio-8-(D)-serine-cyclosporin
3-(2-tert-Butyl-ethylaminoethyl)thio-8-(D)-serine-cyclosporin
3-(2-tert-Butyl-isopropylaminoethyl)thio-8-(D)-serine-cyclosporin
3-(2-Azetidinoethyl)thio-8-(D)-serine-cyclosporin
3-(2-pyrrolidinoethyl)thio-8-(D)-serine-cyclosporin
3-(2-piperidinoethyl)thio-8-(D)-serine-cyclosporin
3-(2-morpholinoethyl)thio-8-(D)-serine-cyclosporin
3-(2-piperazinoethyl)thio-8-(D)-serine-cyclosporin
3-(2-N-methylpiperazinoethyl)thio-8-(D)-serine-cyclosporin
3-(2-N-tert-butylpiperazinoethyl)thio-8-(D)-serine-cyclosporin
3-(3-azetidinyl)thio-8-(D)-serine-cyclosporin
3-(N-methyl-3-azetidinyl)thio-8-(D)-serine-cyclosporin
3-(N-methyl-3-azetidinyl)thio-8-(D)-serine-cyclosporin
3-(N-isopropyl-3-azetidinyl)thio-8-(D)-serine-cyclosporin
3-(3-pyrrolidinyl)thio-8-(D)-serine-cyclosporin
3-(N-methyl-3-pyrrolidinyl)thio-8-(D)-serine-cyclosporin
3-(N-methyl-3-pyrrolidinyl)thio-8-(D)-serine-cyclosporin
3-(N-isopropyl-3-pyrrolidinyl)thio-8-(D)-serine-cyclosporin
3-(4-piperidinyl)thio-8-(D)-serine-cyclosporin
3-(N-methyl-4-piperidinyl)thio-8-(D)-serine-cyclosporin
3-(N-methyl-4-piperidinyl)thio-8-(D)-serine-cyclosporin
3-(N-isopropyl-4-piperidinyl)thio-8-(D)-serine-cyclosporin
3-(2-Hydroxyethoxy)-cyclosporin
3-(3-Hydroxypropoxy)-cyclosporin
3-(2-Chloroethoxy)-cyclosporin
3-(2-Bromoethoxy)-cyclosporin
3-(2-Hydroxyethoxy)-cyclosporin
3-(3-Chloropropoxy)-cyclosporin
3-(3-Bromopropoxy)-cyclosporin
3-(3-Hydroxypropoxy)-cyclosporin
3-(3-Chlorobutoxy)-cyclosporin
3-(3-Bromobutoxy)-cyclosporin
3-(2-Aminoethoxy)-cyclosporin
3-(2-Methylaminoethoxy)-cyclosporin
3-(2-Dimethylaminoethoxy)-cyclosporin
3-(2-Ethylaminoethoxy)-cyclosporin
3-(2-Ethyl-N-methylaminoethoxy)-cyclosporin
3-(2-Dimethylaminoethoxy)-cyclosporin
3-(2-n-Propylaminoethoxy)-cyclosporin
3-(2-Isopropylaminoethoxy)-cyclosporin
3-(2-Cyclopropylaminoethoxy)-cyclosporin
3-(2-n-Propyl-ethylaminoethoxy-cyclosporin
3-(2-n-Propyl-ethylaminoethoxy)-cyclosporin
3-(2-Methyl-isopropylaminoethoxy)-cyclosporin
3-(2-Cyclopropylaminoethoxy)-cyclosporin
3-(2-Ethyl-isopropylaminoethoxy)-cyclosporin
3-(2-Diisopropylaminoethoxy)-cyclosporin
3-(2-n-Propyl-isopropylaminoethoxy)-cyclosporin
3-(2-n-Butylaminoethoxy)cyclosporin
3-(2-sec-Butylaminoethoxy)-cyclosporin
3-(2-Isobutylaminoethoxy)-cyclosporin
3-(2-tert-Butylaminoethoxy)-cyclosporin
3-(2-n-Butyl-methylaminoethoxy)-cyclosporin
3-(2-n-Butyl-ethylaminoethoxy)-cyclosporin
3-(2-n-Butyl-isopropylaminoethoxy)cyclosporin
3-(2-sec-Butyl-methylaminoethoxy)-cyclosporin
3-(2-sec-Butyl-ethylaminoethoxy)-cyclosporin
3-(2-sec-Butyl-isopropylaminoethoxy)-cyclosporin
3-(2-tert-Butyl-methylaminoethoxy)-cyclosporin
3-(2-tert-Butyl-ethylaminoethoxy)-cyclosporin
3-(2-tert-Butyl-isopropylaminoethoxy)-cyclosporin
3-(2-Azetidinoethoxy)-cyclosporin
3-(2-pyrrolidinoethoxy)-cyclosporin
3-(2-piperidinoethoxy)-cyclosporin
3-(2-morpholinoethoxy)-cyclosporin 3-(2-piperidinoethoxy)-cyclosporin
3-(2-N-methylpiperazinoethoxy)-cyclosporin
3-(2-N-methylpiperazinoethoxy)-cyclosporin
3-(2-N-isopropylpiperazinoethoxy)-cyclosporin
3-(3-azetidinyloxy)-cyclosporin
3-(N-methyl-3-azetidinyloxy)-cyclosporin
3-(N-isopropyl-3-azetidinyloxy)-cyclosporin
3-(N-tert-butyl-3-azetidinyloxy)-cyclosporin
3-(3-pyrrolidinyloxy)-cyclosporin
3-(N-methyl-3-pyrrolidinyloxy)-cyclosporin
3-(N-tert-butyl-3-pyrrolidinyloxy)-cyclosporin
3-(N-isopropyl-3-pyrrolidinyloxy)-cyclosporin
3-(4-piperidinyloxy)-cyclosporin
3-(N-methyl-4-piperidinyloxy)-cyclosporin
3-(N-isopropyl-4-piperidinyloxy)-cyclosporin
3-(N-tert-butyl-4-piperidinyloxy)-cyclosporin
3-(2-Hydroxyethoxy)-2-valine-cyclosporin
3-(3-Hydroxypropoxy)-2-valine-cyclosporin
3-(2-Chloroethoxy)-2-valine-cyclosporin
3-(2-Bromoethoxy)-2-valine-cyclosporin
3-(2-Hydroxyethoxy)-2-valine-cyclosporin
3-(3-Chloropropoxy)-2-valine-cyclosporin
3-(3-Bromopropoxy)-2-valine-cyclosporin
3-(3-Hydroxypropoxy)-2-valine-cyclosporin
3-(3-Chlorobutoxy)-2-valine-cyclosporin
3-(3-Bromobutoxy)-2-valine-cyclosporin3-(2-Aminoethoxy)-2-valine-cyclosporin
3-(2-Methylaminoethoxy)-2-valine-cyclosporin
3-(2-Dimethylaminoethoxy)-2-valine-cyclosporin
3-(2-Ethylaminoethoxy)-2-valine-cyclosporin
3-(2-Ethyl-N-methylaminoethoxy)-2-valine-cyclosporin
3-(2-Dimethylaminoethoxy)-2-valine-cyclosporin
3-(2-n-Propylaminoethoxy)-2-valine-cyclosporin
3-(2-Isopropylaminoethoxy)-2-valine-cyclosporin
3-(2-Cyclopropylaminoethoxy)-2-valine-cyclosporin
3-(2-n-Propyl-methylaminoethoxy)-2-valine-cyclosporin
3-(2-n-Propyl-ethylaminoethoxy)-2-valine-cyclosporin
3-(2-Methyl-isopropylaminoethoxy)-2-valine-cyclosporin
3-(2-Cyclopropylaminoethoxy)-2-valine-cyclosporin
3-(2-Ethyl-isopropylaminoethoxy)-2-valine-cyclosporin
3-(2-Diisopropylaminoethoxy)-2-valine-cyclosporin
3-(2-n-Propyl-isopropylaminoethoxy)-2-valine-cyclosporin
3-(2-n-Butylaminoethoxy)-2-valine-cyclosporin
3-(2-sec-Butylaminoethoxy)-2-valine-cyclosporin
3-(2-Isobutylaminoethoxy)-2-valine-cyclosporin
3-(2-tert-Butylaminoethoxy)-2-valine-cyclosporin
3-(2-n-Butyl-methylaminoethoxy)-2-valine-cyclosporin
3-(2-n-Butyl-ethylaminoethoxy)-2-valine-cyclosporin
3-(2-n-Butyl-isopropylaminoethoxy)-2-valine-cyclosporin
3-(2-sec-Butyl-methylaminoethoxy)-2-valine-cyclosporin
3-(2-sec-Butyl-ethylaminoethoxy)-2-valine-cyclosporin
3-(2-sec-Butyl-isopropylaminoethoxy)-2-valine-cyclosporin
3-(2-tert-Butyl-methylaminoethoxy)-2-valine-cyclosporin
3-(2-tert-Butyl-ethylaminoethoxy)-2-valine-cyclosporin
3-(2-tert-Butyl-isopropylaminoethoxy)-2-valine-cyclosporin
3-(2-Azetidinoethoxy)-2-valine-cyclosporin
3-(2-pyrrolidinoethoxy)-2-valine-cyclosporin
3-(2-piperidinoethoxy)-2-valine-cyclosporin
3-(2-morpholinoethoxy)-2-valine-cyclosporin
3-(2-piperidinoethoxy)-2-valine-cyclosporin
3-(2-N-methylpiperazinoethoxy)-2-valine-cyclosporin
3-(2-N-methylpiperazinoethoxy)-2-valine-cyclosporin
3-(2-N-isopropylpiperazinoethoxy)-2-valine-cyclosporin
3-(3-azetidinyloxy)-2-valine-cyclosporin
3-(N-methyl-3-azetidinyloxy)-2-valine-cyclosporin
3-(N-isopropyl-3-azetidinyloxy)-2-valine-cyclosporin
3-(N-tert-butyl-3-azetidinyloxy)-2-valine-cyclosporin
3-(3-pyrrolidinyloxy)-2-valine-cyclosporin
3-(N-methyl-3-pyrrolidinyloxy)-2-valine-cyclosporin
3-(N-tert-butyl-3-pyrrolidinyloxy)-2-valine-cyclosporin
3-(N-isopropyl-3-pyrrolidinyloxy)-2-valine-cyclosporin
3-(4-piperidinyloxy)-2-valine-cyclosporin
3-(N-methyl-4-piperidinyloxy)-2-valine-cyclosporin
3-(N-isopropyl-4-piperidinyloxy)-2-valine-cyclosporin
3-(N-tert-butyl-4-piperidinyloxy)-2-valine-cyclosporin
3-(2-Hydroxyethoxy)-4-(gamma-hydroxy-methylleucine)-cyclosporin
3-(3-Hydroxypropoxy)-4-(gamma-hydroxy-methylleucine)-cyclosporin
3-(2-Chloroethoxy)-4-(gamma-hydroxy-methylleucine)-cyclosporin
3-(2-Bromoethoxy)-4-(gamma-hydroxy-methylleucine)-cyclosporin
3-(2-Hydroxyethoxy)-4-(gamma-hydroxy-methylleucine)-cyclosporin
3-(3-Chloropropoxy)-4-(gamma-hydroxy-methylleucine)-cyclosporin
3-(3-Bromopropoxy)-4-(gamma-hydroxy-methylleucine)-cyclosporin
3-(3-Hydroxypropoxy)-4-(gamma-hydroxy-methylleucine)-cyclosporin
3-(3-Chlorobutoxy)-4-(gamma-hydroxy-methylleucine)-cyclosporin
3-(3-Bromobutoxy)-4-(gamma-hydroxy-methylleucine)-cyclosporin
3-(2-Aminoethoxy)-4-(gamma-hydroxy-methylleucine)-cyclosporin
3-(2-Methylaminoethoxy)-4-(gamma-hydroxy-methylleucine)-cyclosporin
3-(2-Dimethylaminoethoxy)-4-(gamma-hydroxy-methylleucine)-cyclosporin
3-(2-Ethylaminoethoxy)-4-(gamma-hydroxy-methylleucine)-cyclosporin
3-(2-Ethyl-N-methylaminoethoxy)-4-(gamma-hydroxy-methylleucine)-cyclosporin
3-(2-Dimethylaminoethoxy)-4-(gamma-hydroxy-methylleucine)-cyclosporin
3-(2-n-Propylaminoethoxy)-4-(gamma-hydroxy-methylleucine)-cyclosporin
3-(2-Isopropylaminoethoxy)-4-(gamma-hydroxy-methylleucine)-cyclosporin
3-(2-Cyclopropylaminoethoxy)-4-(gamma-hydroxy-methylleucine)-cyclosporin
3-(2-n-Propyl-methylaminoethoxy)-4-(gamma-hydroxy-methylleucine)-cyclosporin
3-(2-n-Propyl-ethylaminoethoxy)-4-(gamma-hydroxy-methylleucine)-cyclosporin
3-(2-Methyl-isopropylaminoethoxy)-4-(gamma-hydroxy-methylleucine)-cyclosporin
3-(2-Cyclopropylaminoethoxy)-4-(gamma-hydroxy-methylleucine)-cyclosporin
3-(2-Ethyl-isopropylaminoethoxy)-4-(gamma-hydroxy-methylleucine)-cyclosporin
3-(2-Diisopropylaminoethoxy)-4-(gamma-hydroxy-methylleucine)-cyclosporin
3-(2-n-Propyl-isopropylaminoethoxy)-4-(gamma-hydroxy-methylleucine)-cyclosporin
3-(2-n-Butylaminoethoxy)-4-(gamma-hydroxy-methylleucine)-cyclosporin
3-(2-sec-Butylaminoethoxy)-4-(gamma-hydroxy-methylleucine)-cyclosporin
3-(2-Isobutylaminoethoxy)-4-(gamma-hydroxy-methylleucine)-cyclosporin 3-(2-tert-Butylaminoethoxy)-4-(gamma-hydroxy-methylleucine)-cyclosporin
3-(2-n-Butyl-methylaminoethoxy)-4-(gamma-hydroxy-methylleucine)-cyclosporin
3-(2-n-Butyl-ethylaminoethoxy)-4-(gamma-hydroxy-methylleucine)-cyclosporin
3-(2-n-Butyl-isopropylaminoethoxy)-4-gamma-hydroxy-methylleucine)-cyclosporin
3-(2-sec-Butyl-methylaminoethoxy)-4-(gamma-hydroxy-methylleucine)-cyclosporin
3-(2-sec-Butyl-methylaminoethoxy)-4-(gamma-hydroxy-methylleucine)-cyclosporin
3-(2-sec-Butyl-isopropylaminoethoxy)-4-(gamma-hydroxy-methylleucine)-cyclosporin
3-(2-tert-Butyl-methylaminoethoxy)-4-(gamma-hydroxy-methylleucine)-cyclosporin
3-(2-tert-Butyl-ethylaminoethoxy)-4-(gamma-hydroxy-methylleucine)-cyclosporin
3-(2-tert-Butyl-isopropylaminoethoxy)-4-(gamma-hydroxy-methylleucine)-cyclosporin
3-(2-Azetidinoethoxy)-4-(gamma-hydroxy-methylleucine)-cyclosporin
3-(2-pyrrolidinoethoxy)-4-(gamma-hydroxy-methylleucine)-cyclosporin
3-(2-piperidinoethoxy)-4-(gamma-hydroxy-methylleucine)-cyclosporin
3-(2-morpholinoethoxy)-4-(gamma-hydroxy-methylleucine)-cyclosporin
3-(2-piperidinoethoxy)-4-(gamma-hydroxy-methylleucine)-cyclosporin
3-(2-N-methylpiperazinoethoxy)-4-(gamma-hydroxy-methylleucine)-cyclosporin
3-(2-N-methylpiperazinoethoxy)-4-(gamma-hydroxy-methylleucine)-cyclosporin
3-(2-N-isopropylpiperazinoethoxy)-4-(gamma-hydroxy-methylleucine)-cyclosporin
3-(3-azetidinyloxy)-4-(gamma-hydroxy-methylleucine)-cyclosporin
3-(N-methyl-3-azetidinyloxy)-4-(gamma-hydroxy-methylleucine)-cyclosporin
3-(N-isopropyl-3-azetidinyloxy)-4-(gamma-hydroxy-methylleucine)-cyclosporin
3-(N-tert-butyl-3-azetidinyloxy)-4-(gamma-hydroxy-methylleucine)-cyclosporin
3-(3-pyrrolidinyloxy)-4-(gamma-hydroxy-methylleucine)-cyclosporin
3-(N-methyl-3-pyrrolidinyloxy)-4-(gamma-hydroxy-methylleucine)-cyclosporin
3-(N-tert-butyl-3-pyrrolidinyloxy)-4-(gamma-hydroxy-methylleucine)-cyclosporin
3-(N-isopropyl-3-pyrrolidinyloxy)-4-(gamma-hydroxy-methylleucine)-cyclosporin
3-(4-piperidinyloxy)-4-(gamma-hydroxy-methylleucine)-cyclosporin
3-(N-methyl-4-piperidinyloxy)-4-(gamma-hydroxy-methylleucine)-cyclosporin
3-(N-isopropyl-4-piperidinyloxy)-4-(gamma-hydroxy-methylleucine)-cyclosporin
3-(N-tert-butyl4-piperidinyloxy)-4-(gamma-hydroxy-methylleucine)-cyclosporin
3-(2-Hydroxyethoxy)-2-norvaline-cyclosporin
3-(3-Hydroxypropoxy)-2-norvaline-cyclosporin
3-(2-Chloroethoxy)-2-norvaline-cyclosporin
3-(2-Bromoethoxy)-2-norvaline-cyclosporin
3-(2-Hydroxyethoxy)-2-norvaline-cyclosporin
3-(3-Chloropropoxy)-2-norvaline-cyclosporin
3-(3-Bromopropoxy)-2-norvaline-cyclosporin
3-(3-Hydroxypropoxy)-2-norvaline-cyclosporin
3-(3-Chlorobutoxy)-2-norvaline-cyclosporin
3-(3-Bromobutoxy)-2-norvaline-cyclosporin
3-(2-Aminoethoxy)-2-norvaline-cyclosporin
3-(2-Methylaminoethoxy)-2-norvaline-cyclosporin
3-(2-Dimethylaminoethoxy)-2-norvaline-cyclosporin
3-(2-Ethylaminoethoxy)-2-norvaline-cyclosporin
3-(2-Ethyl-N-methylaminoethoxy)-2-norvaline-cyclosporin
3-(2-Dimethylaminoethoxy)-2-norvaline-cyclosporin
3-(2-n-Propylaminoethoxy)-2-norvaline-cyclosporin
3-(2-Isopropylaminoethoxy)-2-norvaline-cyclosporin
3-(2-Cyclopropylaminoethoxy)-2-norvaline-cyclosporin
3-(2-n-Propyl-Methylaminoethoxy)-2-norvaline-cyclosporin
3-(2-n-Propyl-ethylaminoethoxy)-2-norvaline-cyclosporin
3-(2-Methyl-isopropylaminoethoxy)-2-norvaline-cyclosporin
3-(2-Cyclopropylaminoethoxy)-2-norvaline-cyclosporin
3-(2-Ethyl-isopropylaminoethoxy)-2-norvaline-cyclosporin
3-(2-Diisopropylaminoethoxy)-2-norvaline-cyclosporin
3-(2-n-Propyl-isopropylaminoethoxy)-2-norvaline-cyclosporin
3-(2-n-Butylaminoethoxy)-2-norvaline-cyclosporin
3-(2-sec-Butylaminoethoxy)-2-norvaline-cyclosporin
3-(2-Isobutylaminoethoxy)-2-norvaline-cyclosporin
3-(2-tert-Butylaminoethoxy)-2-norvaline-cyclosporin
3-(2-n-Butyl-methylaminoethoxy)-2-norvaline-cyclosporin
3-(2-n-Butyl-ethylaminoethoxy)-2-norvaline-cyclosporin
3-(2-n-Butyl-isopropylaminoethoxy)-2-norvaline-cyclosporin
3-(2-sec-Butyl-methylaminoethoxy)-2-norvaline-cyclosporin
3-(2-sec-Butyl-ethylaminoethoxy)-2-norvaline-cyclosporin
3-(2-sec-Butyl-isopropylaminoethoxy)-2-norvaline-cyclosporin
3-(2-tert-Butyl-methylaminoethoxy)-2-norvaline-cyclosporin
3-(2-tert-Butyl-ethylaminoethoxy)-2-norvaline-cyclosporin
3-(2-tert-Butyl-isopropylaminoethoxy)-2-norvaline-cyclosporin
3-(2-Azetidinoethoxy)-2-norvaline-cyclosporin
3-(2-pyrrolidinoethoxy)-2-norvaline-cyclosporin
3-(2-piperidinoethoxy)-2-norvaline-cyclosporin
3-(2-morpholinoethoxy)-2-norvaline-cyclosporin
3-(2-piperidinoethoxy)-2-norvaline-cyclosporin
3-(2-N-methylpiperazinoethoxy)-2-norvaline-cyclosporin
3-(2-N-methylpiperazinoethoxy)-2-norvaline-cyclosporin
3-(2-N-isopropylpiperazinoethoxy)-2-norvaline-cyclosporin
3-(3-azetidinyloxy)-2-norvaline-cyclosporin
3-(N-methyl-3-azetidinyloxy)-2-norvaline-cyclosporin
3-(N-isopropyl-3-azetidinyloxy)-2-norvaline-cyclosporin
3-(N-tert-butyl-3-azetidinyloxy)-2-norvaline-cyclosporin
3-(3-pyrrolidinyloxy)-2-norvaline-cyclosporin
3-(N-methyl-3-pyrrolidinyloxy)-2-norvaline-cyclosporin
3-(N-tert-butyl-3-pyrrolidinyloxy)-2-norvaline-cyclosporin
3-(N-isopropyl-3-pyrrolidinyloxy)-2-norvaline-cyclosporin
3-(4-piperidinyloxy)-2-norvaline-cyclosporin
3-(N-methyl-4-piperidinyloxy)-2-norvaline-cyclosporin
3-(N-isopropyl-4-piperidinyloxy)-2-norvaline-cyclosporin
3-(N-tert-butyl4-piperidinyloxy)-2-norvaline-cyclosporin
3-(2-Hydroxyethoxy)-4-methylvaline-cyclosporin
3-(3-Hydroxypropoxy)-4-methylvaline-cyclosporin
3-(2-Chloroethoxy)-4-methylvaline-cyclosporin
3-(2-Bromoethoxy)-4-methylvaline-cyclosporin
3-(2-Hydroxyethoxy)-4-methylvaline-cyclosporin
3-(3-Chloropropoxy)-4-methylvaline-cyclosporin 3-(3-Bromopropoxy)-4-methylvaline-cyclosporin
3-(3-Hydroxypropoxy)-4-methylvaline-cyclosporin
3-(3-Chlorobutoxy)-4-methylvaline-cyclosporin
3-(3-Bromobutoxy)-4-methylvaline-cyclosporin
3-(2-Aminoethoxy)-4-methylvaline-cyclosporin
3-(2-Methylaminoethyl)-4-methylvaline-cyclosporin
3-(2-Dimethylaminoethoxy)-4-methylvaline-cyclosporin
3-(2-Ethylaminoethoxy)-4-methylvaline-cyclosporin
3-(2-Ethyl-N-methylaminoethoxy)-4-methylvaline-cyclosporin
3-(2-Dimethylaminoethoxy)-4-methylvaline-cyclosporin
3-(2-n-Propylaminoethoxy)-4-methylvaline-cyclosporin
3-(2Isopropylaminoethoxy)-4-methylvaline-cyclosporin
3-(2-Cyclopropylaminoethoxy)-4-methylvaline-cyclosporin
3-(2-n-Propyl-Methylaminoethoxy)-4-methylvaline-cyclosporin
3-(2-n-Propyl-ethylaminoethoxy)-4-methylvaline-cyclosporin
3-(2-Methyl-isopropylaminoethoxy)-4-methylvaline-cyclosporin
3-(2-Cyclopropylaminoethoxy)-4-methylvaline-cyclosporin
3-(2-Ethyl-isopropylaminoethoxy)-4-methylvaline-cyclosporin
3-(2-Diisopropylaminoethoxy)-4-methylvaline-cyclosporin
3-(2-n-Propyl-isopropylaminoethoxy)-4-methylvaline-cyclosporin
3-(2-n-Butylaminoethoxy)-4-methylvaline-cyclosporin
3-(2-sec-Butylaminoethoxy)-4-methylvaline-cyclosporin
3-(2-Isobutylaminoethoxy)-4-methylvaline-cyclosporin
3-(2-tert-Butylaminoethoxy)-4-methylvaline-cyclosporin
3-(2-n-Butyl-methylaminoethoxy)-4-methylvaline-cyclosporin
3-(2-n-Butyl-ethylaminoethoxy)-4-methylvaline-cyclosporin
3-(2-n-Butyl-isopropylaminoethoxy)-4-methylvaline-cyclosporin
3-(2-sec-Butyl-methylaminoethoxy)-methylvaline-cyclosporin
3-(2-sec-Butyl-ethylaminoethoxy)-4-methylvaline-cyclosporin
3-(2-sec-Butyl-isopropylaminoethoxy)-4-methylvaline-cyclosporin
3-(2-tert-Butyl-methylaminoethoxy)-4-methylvaline-cyclosporin
3-(2-tert-Butyl-ethylaminoethoxy)-methylvaline-cyclosporin
3-(2-tert-Butyl-isopropylaminoethoxy)-4-methylvaline-cyclosporin
3-(2-Azetidinoethoxy)-methylvaline-cyclosporin
3-(2-pyrrolidinoethoxy)-4-methylvaline-cyclosporin
3-(2-piperidinoethoxy)-4-methylvaline-cyclosporin
3-(2-morpholinoethoxy)-4-methylvaline-cyclosporin
3-(2-piperidinoethoxy)-4-methylvaline-cyclosporin
3-(2-N-methylpiperazinoethoxy)-methylvaline-cyclosporin
3-(2-N-methylpiperazinoethoxy)-4-methylvaline-cyclosporin
3-(2-N-isopropylpiperazinoethoxy)-4-methylvaline-cyclosporin
3-(3-azetidinyloxy)-4-methylvaline-cyclosporin
3-(N-methyl-3-azetidinyloxy)-4-methylvaline-cyclosporin
3-(N-isopropyl-3-azetidinyloxy)-4-methylvaline-cyclosporin
3-(N-tert-butyl-3-azetidinyloxy)-4-methylvaline-cyclosporin
3-(3-pyrrolidinyloxy)-4-methylvaline-cyclosporin
3-(N-methyl-3-pyrrolidinyloxy)-4-methylvaline-cyclosporin
3-(N-tert-butyl-3-pyrrolidinyloxy)-4-methylvaline-cyclosporin
3-(N-isopropyl-3-pyrrolidinyloxy)-4-methylvaline-cyclosporin
3-(4-piperidinyloxy)-4-methylvaline-cyclosporin
3-(N-methyl-4-piperidinyloxy)-4-methylvaline-cyclosporin
3-(N-isopropyl-4-piperidinyloxy)-4-methylvaline-cyclosporin
3-(N-tert-butyl-4-piperidinyloxy)-4-methylvaline-cyclosporin
3-(2-Hydroxyethoxy)-4-methylisoleucine-cyclosporin
3-(3-Hydroxypropoxy)-4-methylisoleucine-cyclosporin
3-(2-Chloroethoxy)-4-methylisoleucine-cyclosporin
3-(2-Bromoethoxy)-4-methylisoleucine-cyclosporin
3-(2-Hydroxyethoxy)-4-methylisoleucine-cyclosporin
3-(3-Chloropropoxy)-4-methylisoleucine-cyclosporin
3-(3-Bromopropoxy)-4-methylisoleucine-cyclosporin
3-(3-Hydroxypropoxy)-4-methylisoleucine-cyclosporin
3-(3-Chlorobutoxy)-4-methylisoleucine-cyclosporin
3-(3-Bromobutoxy)-4-methylisoleucine-cyclosporin
3-(2-Aminoethoxy)-4-methylisoleucine-cyclosporin
3-(2-Methylaminoethoxy)-4-methylisoleucine-cyclosporin
3-(2-Dimethylaminoethoxy)-4-methylisoleucine-cyclosporin
3-(2-Ethylaminoethoxy)-4-methylisoleucine-cyclosporin
3-(2-Ethyl-N-methylaminoethoxy)-4-methylisoleucine-cyclosporin
3-(2-Dimethylaminoethoxy)-4-methylisoleucine-cyclosporin
3-(2-n-Propylaminoethoxy)-4-methylisoleucine-cyclosporin
3-(2-Isopropylaminoethoxy)-4-methylisoleucine-cyclosporin
3-(2-Cyclopropylaminoethoxy)-4-methylisoleucine-cyclosporin
3-(2-n-Propyl-Methylaminoethoxy)-4-methylisoleucine-cyclosporin
3-(2-n-Propyl-ethylaminoethoxy)-4-methylisoleucine-cyclosporin
3-(2-Methyl-isopropylaminoethoxy)-4-methylisoleucine-cyclosporin
3-(2-Cyclopropylaminoethoxy)-4-methylisoleucine-cyclosporin
3-(2-Ethyl-isopropylaminoethoxy)-4-methylisoleucine-cyclosporin
3-(2-Diisopropylaminoethoxy)-4-methylisoleucine-cyclosporin
3-(2-n-Propyl-isopropylaminoethoxy)-4-methylisoleucine-cyclosporin
3-(2-n-Butylaminoethoxy)-4-methylisoleucine-cyclosporin
3-(2-sec-Butylaminoethoxy)-4-methylisoleucine-cyclosporin
3-(2-Isobutylaminoethoxy)-4-methylisoleucine-cyclosporin
3-(2-tert-Butylaminoethoxy)-4-methylisoleucine-cyclosporin
3-(2-n-Butyl-methylaminoethoxy)-4-methylisoleucine-cyclosporin
3-(2-n-Butyl-ethylaminoethoxy)-4-methylisoleucine-cyclosporin
3-(2-n-Butyl-isopropylaminoethoxy)-4-methylisoleucine-cyclosporin
3-(2-sec-Butyl-methylaminoethoxy)-4-methylisoleucine-cyclosporin
3-(2-sec-Butyl-ethylaminoethoxy)-4-methylisoleucine-cyclosporin
3-(2-sec-Butyl-isopropylaminoethoxy)-4-methylisoleucine-cyclosporin 3-(2-tert-Butyl-methylaminoethoxy)-4-methylisoleucine-cyclosporin
3-(2-tert-Butyl-ethylaminoethoxy)-4-methylisoleucine-cyclosporin
3-(2-tert-Butyl-isopropylaminoethoxy)-4-methylisoleucine-cyclosporin
3-(2-Azetidinoethoxy)-4-methylisoleucine-cyclosporin
3-(2-pyrrolidinoethoxy)-4-methylisoleucine-cyclosporin
3-(2-piperidinoethoxy)-4-methylisoleucine-cyclosporin
3-(2-morpholinoethoxy)-4-methylisoleucine-cyclosporin
3-(2-piperidinoethoxy)-4-methylisoleucine-cyclosporin
3-(2-N-methylpiperazinoethoxy)-4-methylisoleucine-cyclosporin
3-(2-N-methylpiperazinoethoxy)-4-methylisoleucine-cyclosporin
3-(2-N-isopropylpiperazinoethoxy)-4-methylisoleucine-cyclosporin
3-(3-azetidinyloxy)-4-methylisoleucine-cyclosporin
3-(N-methyl-3-azetidinyloxy)-4-methylisoleucine-cyclosporin
3-(N-isopropyl-3-azetidinyloxy)-4-methylisoleucine-cyclosporin
3-(N-tert-butyl-3-azetidinyloxy)-4-methylisoleucine-cyclosporin
3-(3-pyrrolidinyloxy)-4-methylisoleucine-cyclosporin
3-(N-methyl-3-pyrrolidinyloxy)-4-methylisoleucine-cyclosporin
3-(N-tert-butyl-3-pyrrolidinyloxy)-4-methylisoleucine-cyclosporin
3-(N-isopropyl-3-pyrrolidinyloxy)-4-methylisoleucine-cyclosporin
3-(4-piperidinyloxy)-4-methylisoleucine-cyclosporin
3-(N-methyl-4-piperidinyloxy)-4-methylisoleucine-cyclosporin
3-(N-isopropyl-4-piperidinyloxy)-4-methylisoleucine-cyclosporin
3-(N-tert-butyl4-piperidinyloxy)-4-methylisoleucine-cyclosporin
3-(2-Hydroxyethoxy)-8-(D)-serine-cyclosporin
3-(3-Hydroxypropoxy)-8-(D)-serine-cyclosporin
3-(2-Chloroethoxy)-8-(D)-serine-cyclosporin
3-(2-Bromoethoxy)-8-(D)-serine-cyclosporin
3-(2-Hydroxyethoxy)-8-(D)-serine-cyclosporin
3-(3-Chloropropoxy)-8-(D)-serine-cyclosporin
3-(3-Bromopropoxy)-8-(D)-serine-cyclosporin
3-(3-Hydroxypropoxy)-8-(D)-serine-cyclosporin
3-(3-Chlorobutoxy)-8-(D)-serine-cyclosporin
3-(3-Bromobutoxy)-8-(D)-serine-cyclosporin
3-(2-Aminoethoxy)-8-(D)-serine-cyclosporin
3-(2-Methylaminoethoxy)-8-(D)-serine-cyclosporin
3-(2-Dimethylaminoethoxy)-8-(D)-serine-cyclosporin
3-(2-Ethylaminoethoxy)-8-(D)-serine-cyclosporin
3-(2-Ethyl-N-methylaminoethoxy)-8-(D)-serine-cyclosporin
3-(2-Dimethylaminoethoxy)-8-(D)-serine-cyclosporin
3-(2-n-Propylaminoethoxy)-8-(D)-serine-cyclosporin
3-(2-Isopropylaminoethoxy)-8-(D)-serine-cyclosporin
3-(2-Cyclopropylaminoethoxy)-8-(D)-serine-cyclosporin
3-(2-n-Propyl-Methylaminoethoxy)-8-(D)-serine-cyclosporin
3-(2-n-Propyl-ethylaminoethoxy)-8-(D)-serine-cyclosporin
3-(2-Methyl-isopropylaminoethoxy)-8-(D)-serine-cyclosporin
3-(2-Cyclopropylaminoethoxy)-8-(D)-serine-cyclosporin
3-(2-Ethyl-isopropylaminoethoxy)-8-(D)-serine-cyclosporin
3-(2-Diisopropylaminoethoxy)-8-(D)-serine-cyclosporin
3-(2-n-Propyl-isopropylaminoethoxy)-8-(D)-serine-cyclosporin
3-(2-n-Butylaminoethoxy)-8-(D)-serine-cyclosporin
3-(2-sec-Butylaminoethoxy)-8-(D)-serine-cyclosporin
3-(2-Isobutylaminoethoxy)-8-(D)-serine-cyclosporin
3-(2-tert-Butylaminoethoxy)-8-(D)-serine-cyclosporin
3-(2-n-Butyl-methylaminoethoxy)-8-(D)-serine-cyclosporin
3-(2-n-Butyl-ethylaminoethoxy)-8-(D)-serine-cyclosporin
3-(2-n-Butyl-isopropylaminoethoxy)-8-(D)-serine-cyclosporin
3-(2-sec-Butyl-methylaminoethoxy)-8-(D)-serine-cyclosporin
3-(2-sec-Butyl-ethylaminoethoxy)-8-(D)-serine-cyclosporin
3-(2-sec-Butyl-isopropylaminoethoxy)-8-(D)-serine-cyclosporin
3-(2-tert-Butyl-methylaminoethoxy)-8-(D)-serine-cyclosporin
3-(2-tert-Butyl-ethylaminoethoxy)-8-(D)-serine-cyclosporin
3-(2-tert-Butyl-isopropylaminoethoxy)-8-(D)-serine-cyclosporin
3-(2-Azetidinoethoxy)-8-(D)-serine-cyclosporin
3-(2-pyrrolidinoethoxy)-8-(D)-serine-cyclosporin
3-(2-piperidinoethoxy)-8-(D)-serine-cyclosporin
3-(2-morpholinoethoxy)-8-(D)-serine-cyclosporin
3-(2-piperidinoethoxy)-8-(D)-serine-cyclosporin
3-(2-N-methylpiperazinoethoxy)-8-(D)-serine-cyclosporin
3-(2-N-methylpiperazinoethoxy)-8-(D)-serine-cyclosporin
3-(2-N-isopropylpiperazinoethoxy)-8-(D)-serine-cyclosporin
3-(3-azetidinyloxy)-8-(D)-serine-cyclosporin
3-(N-methyl-3-azetidinyloxy)-8-(D)-serine-cyclosporin
3-(N-isopropyl-3-azetidinyloxy)-8-(D)-serine-cyclosporin
3-(N-tert-butyl-3azetidinyloxy)-8-(D)-serine-cyclosporin
3-(3-pyrrolidinyloxy)-8-(D)-serine-cyclosporin
3-(N-methyl-3-pyrrolidinyloxy)-8-(D)-serine-cyclosporin
3-(N-tert-butyl-3-pyrrolidinyloxy)-8-(D)-serine-cyclosporin
3-(N-isopropyl-3-pyrrolidinyloxy)-8-(D)-serine-cyclosporin
3-(4-piperidinyloxy)-8-(D)-serine-cyclosporin
3-(N-methyl-4-piperidinyloxy)-8-(D)-serine-cyclosporin
3-(N-isopropyl-4-piperidinyloxy)-8-(D)-serine-cyclosporin
3-(N-tert-butyl-4-piperidinyloxy)-8-(D)-serine-cyclosporin

36. Test for Cyclophilin Binding

To measure the affinity and inhibition of test compounds for cyclophilin, the test described by H. Fliri in "Antibiotics and Antiviral compounds", 1993, Verlag Chemie, K.Krohn, H. A. Kirst, and H. Maag, eds., p 229–240 was used. The activity of the compounds shown in the table is expressed as relative IC50, i.e. IC50 (cyclosporin A)/IC50 (test compound):

| Product of example | Relative IC50 (ng/ml) |
| --- | --- |
| 1 | 0.2 |
| 2 | 0.2 |
| 3 | 0.2 |
| 4 | 0.2 |
| 5 | 0.2 |
| 6 | 0.2 |
| 7 | 0.2 |
| 8 | 0.4 |

-continued

| Product of example | Relative IC50 (ng/ml) |
|---|---|
| 9 | 1 |
| 12 | 1.5 |
| 13 | 1.5 |
| 14 | 2 |
| 15 | 2 |

37. Test for Inhibition Cyclophilin

The test described by G. Fischer et al., Biomed. Biochim. Acta, Vol. 43, 1101–1111 (1984) was used. Specifically, 5 µL of a 1 µM solution of recombinant human cyclophilin 18 was dissolved, at 10,0±0.3° C. in 1250 µL HEPES buffer; α-chymotrypsin was added to give a final concentration of 30 µM. Test compounds were dissolved in DMSO as 10 µM solutions and added to the enzyme solution to give final concentrations of 0.1, 0.5, 1.0, 5.0, 10.0, 50.0, 100.0, 500.0, and 1000 nM concentrations. After 5 minutes preincubation, Succ-Ala-Phe-Pro-Phe-4-nitroanilide (SEQ ID No. 1) was added to give a final concentration of 50 µM. The hydrolysis of the substrate was measured spectrophotometrically at 390–450 nM. The following $IC^{50}$ values were obtained:

| Product of Example | Name | IC50 [nM] |
|---|---|---|
|  | Cyclosporin A | 12.43 ± 0.40 |
| 14 | 3-Methoxy-cyclosporin | 11.57 ± 1.59 |
| 15 | 3-Ethoxy-cyclosporin | 11.13 ± 1.03 |
| 16 | 3-Isopropoxy-cyclosporin | 20.39 ± 1.26 |
| 17 | 3-tert-Butoxy-cyclosporin | 18.94 ± 1.03 |
| 18 | 3-Allyloxy-cyclosporin | 10.15 ± 2.21 |

38. Inhibition of HIV Replication

The inhibitory effect of test compounds on the HIV-induced cytopathic effect on the MT4 T cell line as described by R. Pauwels in J. Virol. Methods, 1988, Vol. 20, pp 309–321 was used. The activity of test compounds is shown in the table:

| Product of example | IC50 (ng/ml) |
|---|---|
| 1 | 450 |
| 2 | 1000 |
| 3 | 1000 |
| 4 | 1000 |
| 5 | 1000 |
| 6 | 1000 |
| 7 | 1000 |
| 8 | 500 |
| 9 | 30 |

-continued

| Product of example | IC50 (ng/ml) |
|---|---|
| 12 | 150 |
| 13 | 150 |
| 14 | 100 |

39. Activity Against *Toxoplasma Gondii*

Using microliter plates, *T. gondii* tachyzoites, strain RH were co-incubated with fibroblasts (MCR5, Bio-Merieux) for 72 hrs in the presence and absence of test compounds *T. gondii* was quantified using an ELISA. The activities of the test compounds are as follows:

| Product of example | Activity against *T. gondii* (IC50, µg/ml) |
|---|---|
| 9 | 0.1 |
| 13 | 1 |
| 14 | 0.6 |
| 15 | 0.6 |

40. Antiinflammatory Activity

The antiinflammatory activity of test compounds was determined by the adjuvent arthritis test described by Pearson, "Arthr. Rheum", 1959, Vol. 2., 440. Test compounds were administered orally as solutions in olive oil and tween 80. Their activity is expressed as ED50 in mg/kg, i.e. the dose effective in reducing the joint swelling by 50%, and is as shown below.

| Product of example | ED50 (mg/kg) |
|---|---|
| 1 | 25 |
| 2 | 25 |
| 3 | 25 |
| 4 | 25 |
| 5 | 25 |
| 6 | 25 |
| 7 | 25 |
| 8 | 25 |
| 9 | 15 |
| 12 | 15 |
| 13 | 15 |
| 14 | 10 |
| 15 | 15 |

What is claimed is:

1. A compound of formula I

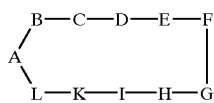

Formula I or a pharmaceutically acceptable salt, thereof, wherein the letters A to L represent residues of the following amino acids:

A (L)-alpha-N-methylamino-beta-hydroxy acid of the formula II

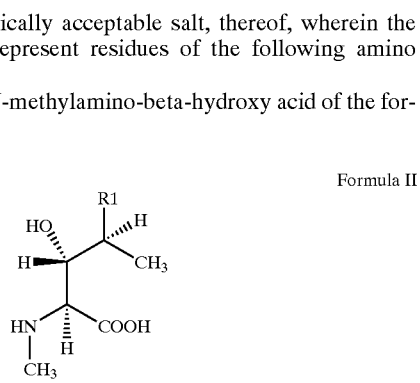

Formula II wherein R1 is (E)-2-butenyl-1,

B alpha-amino-butyric acid, alpha-amino-valerianic acid (norvaline), threonine, or valine, C substituted sarcosine of the formula III

Formula III in which X is O—R3 or O—R10, wherein R3 is hydrogen, methyl, vinyl or allyl, and R10 is selected from the group consisting of ethyl, propyl, isopropyl, n-butyl, sec-butyl, isobutyl, tert-butyl, 1-pentyl, 2-pentyl, 3-pentyl, isopentyl, tert-pentyl, neopentyl, hexyl and isomers of hexyl, cyclopropyl, cyclobutyl, cyclopentyl, cyclohexyl, bicyclo[2.1.1]hexyl, norbornyl, bicyclo[2.2.2]octyl, butenyl, pentenyl, pentadienyl, hexenyl, hexadienyl, formyl, acetyl, propionyl, butyryl, pivaloyl, benzoyl, alkoxycarbonyl, which can be substituted by hydroxy, methoxy, ethoxy, propoxy, isopropoxy, halogen, carboxy, carbamido, amino, methylamino, ethylamino, n-propylamino, isopropylamino, n-butylamino, isobutylamino, sec-butylamino, tert-butylamino, 1-pentylamino, 2-pentylamino, 3-pentylamino, isopentylamino, tert-pentylamino, neopentylamino, hexylamino and isomers of hexylamino, N,N-dimethylamino, N-methyl-N-ethylamino, N,N-diethylamino, N-propyl-N-methylamino, N-methyl-N-isopropylamino, dipropylamino, diisopropylamino, N-butyl-N-methylamino or an isomer thereof, N-butyl-N-ethylamino or an isomer thereof, N-butyl-N-propylamino or an isomer thereof, N,N-dibutylamino or an isomer thereof, azetidine, pyrrolidine, piperidine, morpholine, piperazine, N'-alkylpiperazine, azabicylo[2.1.1]hexane, azanorbornane, azabicylo[2.2.2]octane, N-formylamino, N-acetylamino, N-tert-butoxycarbonyl-amino, N-benzyloxycarbonyl-amino, N-benzoyl-amino, N-phthaloyl, or C is a residue of the formula VI

[H—N$^+$(CH$_3$)=CH—CO—OH]Y$^-$         Formula VI, wherein Y$^-$ is an anion

D is N-methyl-leucine, N-methyl-valine, or N-methyl-isoleucine,

E is valine,

F is N-methyl-leucine,

G is alanine,

H is glycine, (D)-alanine, (D)-serine, O-hydroxyethyl-(D)-serine,

I, K are N-methyl-leucine, and

L is N-methyl-valine.

2. A composition comprising the compound or pharmaceutically acceptable salt thereof according to claim 1, and a pharmaceutically acceptable carrier or diluent.

3. A method of making the composition according to claim 2, said method comprising (a) combining said compound or pharmaceutically acceptable salt thereof with a pharmaceutically acceptable carrier or diluent to obtain said composition, and (b) recovering said composition.

4. A process for synthesizing the compound according to claim 1, comprising (a) reacting a compound of formula I,

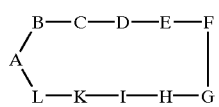

Formula I wherein the letters A, B and D to L have the same meanings as defined in claim 1, and wherein the letter C is a substituted sarcosine of the formula III,

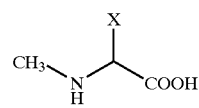

Formula III in which X is SR3 or SR10, wherein R3 and R10 have the same meanings as defined in claim 1,
with a Bronsted or Lewis acid in the presence of an alcohol of formula HO—R3 or HO—R10, wherein R3 and R10 have the same meanings as defined in claim 1, for a time and under conditions effective to form an intermediary cation of formula VI,

[H—N⁺(CH₃)=CH—CO—OH]Y⁻        Formula VI, wherein Y⁻ is an anion, which intermediary cation subsequently reacts with said alcohol; and (b) isolating the compound of formula I in which X is OR3 or OR10, wherein R3 and R10 have the same meanings as defined in claim 1.

5. A process for synthesizing the compound according to claim 1, comprising (a) reacting a compound of formula I,

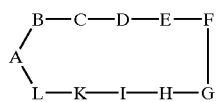

Formula I wherein the letters A, B and D to L have the same meanings as defined in claim 1, and wherein the letter C is a substituted sarcosine of the formula III

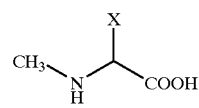

Formula III in which X is SR3 or SR10, wherein R3 and R10 have the same meanings as defined in claim 1,
with a metal salt that has affinity to sulfur, in the presence of an alcohol of formula HO—R3 or HO—R10, wherein R3 and R10 have the same meanings as defined in claim 1, for a time and under conditions effective to form an intermediary cation of formula VI,

[H—N⁺(CH₃)=CH—CO—OH]Y⁻        Formula VI, wherein Y⁻ is an anion, which intermediary cation subsequently reacts with said alcohol; and (b) isolating the compound of formula I in which X is OR3 or OR10, wherein R3 and R10 have the same meanings as defined in claim 1.

6. A method of inhibiting cyclophilins comprising administering the compound or pharmaceutically acceptable salt thereof according to claim 1, to a subject in need thereof for a time and under conditions effective to inhibit said cyclophilins.

7. A method of inhibiting growth of bacteria comprising contacting said bacteria with the compound or pharmaceutically acceptable salt thereof according to claim 1, for a time and under conditions effective to inhibit growth of said bateria.

8. A method of inhibiting growth of bacteria comprising administering the compound or pharmaceutically acceptable salt thereof according to claim 1, to a mammal in need thereof for a time and under conditions effective to inhibit growth of said bacteria.

9. A method of inhibiting replication of human infectivity virus (HIV) comprising contacting HIV with the compound or pharmaceutically acceptable salt thereof according to claim 1, for a time and under conditions effective to inhibit replication of HIV.

10. A method of inhibiting replication of human infectivity virus (HIV) comprising administering the compound or pharmaceutically acceptable salt thereof according to claim 1, to a human subject in need thereof for a time and under conditions effective to inhibit replication of HIV.

11. A method of inhibiting growth of parasites comprising contacting said parasites with the compound or pharmaceutically acceptable salt thereof according to claim 1, for a time and under conditions effective to inhibit growth of said parasites.

12. A method of inhibiting growth of parasites comprising administering the compound or pharmaceutically acceptable salt thereof according to claim 1, to a mammal in need thereof for a time and under conditions effective to inhibit growth of said parasites.

13. A method of inhibiting cyclophilins comprising contacting said cyclophilins with the compound or pharmaceutically acceptable salt thereof according to claim 1, for a time and under conditions effective to inhibit said cyclophilins.

* * * * *

UNITED STATES PATENT AND TRADEMARK OFFICE
CERTIFICATE OF CORRECTION

PATENT NO. : 6,583,265 B1
DATED : June 24, 2003
INVENTOR(S) : Ernst Ellmerer-Muller et al.

It is certified that error appears in the above-identified patent and that said Letters Patent is hereby corrected as shown below:

Column 32,
Line 30, please change "infectivity" to -- immunodeficiency --.
Lines 35 and 36, please change "infectivity" to -- immunodeficiency --.

Signed and Sealed this

Thirtieth Day of December, 2003

JAMES E. ROGAN
*Director of the United States Patent and Trademark Office*

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic Peptide

<400> SEQUENCE: 1

Ala Phe Pro Phe
 1